US010961518B2

(12) United States Patent
Meng et al.

(10) Patent No.: US 10,961,518 B2
(45) Date of Patent: Mar. 30, 2021

(54) MUTANT DNA POLYMERASES

(71) Applicant: Bio-Rad Laboratories, Inc., Hercules, CA (US)

(72) Inventors: Xiangdong Meng, Albany, CA (US); Man Cheng, Danville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 37 days.

(21) Appl. No.: 16/248,442

(22) Filed: Jan. 15, 2019

(65) Prior Publication Data

US 2019/0225951 A1 Jul. 25, 2019

Related U.S. Application Data

(60) Provisional application No. 62/619,394, filed on Jan. 19, 2018.

(51) Int. Cl.
| | |
|---|---|
| *C12N 9/12* | (2006.01) |
| *C12Q 1/686* | (2018.01) |
| *C12Q 1/6876* | (2018.01) |
| *C12N 15/52* | (2006.01) |
| *C12N 15/70* | (2006.01) |
| *C12N 15/74* | (2006.01) |
| *C12N 15/80* | (2006.01) |

(52) U.S. Cl.
CPC .......... *C12N 9/1252* (2013.01); *C12N 15/52* (2013.01); *C12N 15/70* (2013.01); *C12N 15/74* (2013.01); *C12N 15/80* (2013.01); *C12Q 1/686* (2013.01); *C12Q 1/6876* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 6,489,103 | B1 | 12/2002 | Griffiths et al. |
| 7,138,233 | B2 | 11/2006 | Griffiths et al. |
| 7,244,602 | B2 | 7/2007 | Frey et al. |
| 7,252,943 | B2 | 8/2007 | Griffiths et al. |
| 7,507,569 | B2 | 3/2009 | Minning et al. |
| 7,514,210 | B2 | 4/2009 | Holliger et al. |
| 7,582,446 | B2 | 9/2009 | Griffiths et al. |
| 7,638,275 | B2 | 12/2009 | Lewin et al. |
| 7,897,341 | B2 | 3/2011 | Griffiths et al. |
| 8,114,653 | B2 | 2/2012 | Woodgate et al. |
| 8,148,126 | B2 | 4/2012 | Callen et al. |
| 8,153,402 | B2 | 4/2012 | Holliger et al. |
| 8,367,326 | B2 | 2/2013 | Griffiths et al. |
| 8,470,573 | B2 | 6/2013 | Wang et al. |

(Continued)

FOREIGN PATENT DOCUMENTS

WO 2015085230 A1 6/2015

OTHER PUBLICATIONS

NCBI Reference Sequence WP_081641628.1, published Apr. 8, 2017 (Year: 2017).*

(Continued)

*Primary Examiner* — Richard C Ekstrom
(74) *Attorney, Agent, or Firm* — Kilpatrick Townsend and Stockton LLP

(57) ABSTRACT

Mutant Type-A DNA polymerases having increased resistance to one or more polymerization activity inhibitors are provided.

18 Claims, 5 Drawing Sheets

Specification includes a Sequence Listing.

```
SEQ_ID_NO1     ---MLPLFEPKGRVLLVDGHHLAYRNFFTLKGPTTSRGEPVQGVYGFAKSLAKALKEDGD 57
SEQ_ID_NO2     ---MLPLFEPKGRVLLVDGHHLAYRNFFTLKGLTTSRGEPVQGVYGFAKSLAKALKEDGD 57
SEQ_ID_NO3     ---MLPLFEPKGRVLLVDGHHLAYRNFFTLRGLTTSRGEPVQGVYGFAKSLAKALKEDGD 57
SEQ_ID_NO4     ---MLPLFEPKGRVLLVDGHHLAYRNFFTLKGPTTSRGEPVQGVYGFAKSLAKALKEDGD 57
SEQ_ID_NO5     ---MLPLFEPKGRVLLVDGHHLAYRNFFTLKGLTTSRGEPVQGVYGFAKSLAKALKEDGD 57
SEQ_ID_NO6     ---MLPLFEPKGRVLLVDGHHLAHRNFFALKGLTTSRGEPVQGVYGFAKSLLKALKEDGD 57
SEQ_ID_NO7     ---MLPLFEPKGRVLLVDGHHLAYRTFFALKGLTTSRGEPVQGVYGFAKSLLKALKEDGE 57
SEQ_ID_NO8(Taq) MRGMLPLFEPKGRVLLVDGHHLAYRTFHALKGLTTSRGEPVQAVYGFAKSLLKALKEDGD 60
                   ******************:*.*.:*.*  ********.********  *******:

SEQ_ID_NO1     VVIVVFDAKAPSFRHEAYGAYKAGRAPTPEDFPRQLALMKELVDLLGLERLEVPGFEADD 117
SEQ_ID_NO2     VVIVVFDAEAPSFRHEAYGAYKAGRAPTPEDFPRQLALMKELVDLLGLERLEVPGFEADD 117
SEQ_ID_NO3     VVIVVFDAKAPSFRHEAYGAYKAGRAPTPEDFPRQLALMKELVDLLGLERLEVPGFEADD 117
SEQ_ID_NO4     VVIVVFDAKAPSFRHETYGAYKAGRAPTPEDFPRQLALMKELVDLLGLERLEVPGFEADD 117
SEQ_ID_NO5     VVIVVFDAKAPSFRHEAYGAYKAGRAPTPEDFPRQLALMKELVDLLGLERLEVPGFEADD 117
SEQ_ID_NO6     VVIVVFDAKAPSFRHEAYGAYKAGRAPTPEDFPRQLALIKELVDLLGLVRLEVPGFEADD 117
SEQ_ID_NO7     VAIVVFDAKAPSFRHEAYEAYKAGRAPTPEDFPRQLALIKELVDLLGLVRLEVPGFEADD 117
SEQ_ID_NO8(Taq) AVIVVFDAKAPSFRHEAYGGYKAGRAPTPEDFPRQLALIKELVDLLGLARLEVPGYEADD 120
                  .:******.*******:*  ********.********:*********  ****** .****

SEQ_ID_NO1     VLAALAKIAEREGYEVRILTADRDLFQLLSDRIALLHPEGHLITPGWLWERYGLRPEQWV 177
SEQ_ID_NO2     VLAALAKIAEREGYEVRILTADRDLFQLLSDRIAVLHPEGHLITPGWLWERYGLRPEQWV 177
SEQ_ID_NO3     VLAALAKIAEREGYEVRILTADRDLFQLLSDRIAVLHPEGHLITPGWLWERYGLRPEQWV 177
SEQ_ID_NO4     VLAALAKIAEREGYEVRILTADRDLFQLLSDRIAVLHPEGHLITPGWLWERYGLRPEQWV 177
SEQ_ID_NO5     VLAALAKIAEREGYEVRILTADRDLFQLLSDRIAVLHPEGHLITPGWLWERYGLRPEQWV 177
SEQ_ID_NO6     VLATLAKKAEKEGYEVRILTADKDLYQILSDRVHVLHPEGYLITPAWLWEKYGLRPDQWA 177
SEQ_ID_NO7     VLAALAKKAEREGYEVRILSADRDLYQLLSDRIHLLHPEGYLITPAWLWEKYGLRPDQWA 177
SEQ_ID_NO8(Taq) VLASLAKKAEKEGYEVRILTADKDLYQLLSDRIHVLHPEGYLITPAWLWEKYGLRPDQWA 180
                 ***.*** **.*********:**:**:****: .:*****:****.****:***** **.

SEQ_ID_NO1     DFRALAGDPSDNIPGVKGISEKTALKLLKEWGSLENIQKNLAQVKPERVREAIRNNLDXL 237
SEQ_ID_NO2     DFRALAGDPSDNIPGVKGISEKTALKLLKEWGSLENIQKNLAQVKPERVREAIRNNLDXL 237
SEQ_ID_NO3     DFRALTGDPSDNIPGVKGIGEKTALKLLKEWGSLENIQKNLDQVKPERVREAIRNNLDXL 237
SEQ_ID_NO4     DFRALAGDPSDNIPGVKGIGEKTALKLLKEWGSLENIQKNLDQVKPERVREAIRNNLDXL 237
SEQ_ID_NO5     NFRALAGDPSDNIPGVKGIGEKTALKLLKEWGSLENIQKNLDQVKPERVREAIRNNLDXL 237
SEQ_ID_NO6     DYRALTGDESDNLPGVKGIGEKTARKLLEEWGSLEALLKNLDRLKPA-IREKILAHMDDL 236
SEQ_ID_NO7     DYRALTGDESDNLPGVKGIGEKTARKLLEEWGSLEALLKNLDRLKPA-IREKILAHMDDL 236
SEQ_ID_NO8(Taq) DYRALTGDESDNLPGVKGIGEKTARKLLEEWGSLEALLKNLDRLKPA-IREKILAHMDDL 239
                 :***:**  ***.******  ***.***  ***.*****  :  ***  ::**  :**  *  .:*.*

SEQ_ID_NO1     QMSLELSRLRTDLPLEVDFRRRREPDREGLRAFLERLEFGSLLHEFGLLESPKALEEALW 297
SEQ_ID_NO2     QMSLELSRLRTDLPLEVDFRRRRKPDREGLRAFMERLEFDSLLHEFGLLESPKALEEALW 297
SEQ_ID_NO3     QMSLELSRLRTDLPLEVDFRRRREPDREGLRAFLERLEFGSLLHEFGLLESPKALEEALW 297
SEQ_ID_NO4     QMSLELSRLRTDLPLEVDFRRRREPDREGLRAFLERLEFGSLLHEFGLLESPKALEEALW 297
SEQ_ID_NO5     QMSLELSCLRTDLPLEVDFRRRREPDREGLRAFLERLEFGSLLHEFGLLESPKALEEALW 297
SEQ_ID_NO6     KLSWDPAKVRTDLPLEVDFAKRREPDRERLRAFLERLEFGSLLHEFGLLESPKALEEALW 296
SEQ_ID_NO7     KLSWDPAKVRTDLPLEVDFAKRREPDRERLRAFLERLEFGSLLHEFGLLESPKALEEAPW 296
SEQ_ID_NO8(Taq) KLSWDLAKVRTDLPLEVDFAKRREPDRERLRAFLERLEFGSLLHEFGLLESPKALEEAPW 299
                 :.*  :  :  .********* ::****  *:****:********************** *

SEQ_ID_NO1     PPPEGAFVGFVLSRKEPMWADLLALAAARGGRVHRAPEPYKALRDLKEARGLLAKDLSVL 357
SEQ_ID_NO2     PPPEGAFVGFVLSRKEPMWADLLALAAARGGRVHRAPEPYKALRDLKEARGLLAKDLSVL 357
SEQ_ID_NO3     PPPEGAFVGFVLSRKEPMWADLLALAAARGGRVHRAPEPYKALRDLKEARGLLAKDLSVL 357
SEQ_ID_NO4     PPPEGAFVGFVLSRKEPMWADLLALAAARGGRVHRAPEPYKALRDLKEARGLLAKDLSVL 357
SEQ_ID_NO5     PPPEGAFVGFVLSRKEPMWADLLALAAARGGRVHRAPEPYKALRDLKEARGLLAKDLSVL 357
SEQ_ID_NO6     PPPEGAFVGFVLSRKEPMWADLLALAAARGGRVHRAPEPYKALRDLKEARGLLAKDLSVL 356
SEQ_ID_NO7     PPPEGAFVGFVLSRKEPMWADLLALAAARGGRVHRAPEPYKALRDLKEARGLLAKDLSVL 356
SEQ_ID_NO8(Taq) PPPEGAFVGFVLSRKEPMWADLLALAAARGGRVHRAPEPYKALRDLKEARGLLAKDLSVL 359
                 ************************************************************
```

(56) References Cited

U.S. PATENT DOCUMENTS

| | | |
|---|---|---|
| 8,481,685 B2 | 7/2013 | Bourn et al. |
| 9,017,979 B2 | 4/2015 | Bauer et al. |
| 9,096,835 B2 | 8/2015 | Holliger et al. |
| 9,145,550 B2 | 9/2015 | Vander Horn et al. |
| 9,228,179 B2 | 1/2016 | Holliger et al. |
| 9,365,839 B2 | 6/2016 | Hendricks et al. |
| 9,388,396 B2 | 7/2016 | Faurholm et al. |
| 9,523,085 B2 | 12/2016 | Hogrefe et al. |
| 9,528,106 B2 | 12/2016 | Griffiths et al. |
| 9,688,969 B2 | 6/2017 | Vander Horn et al. |
| 9,758,773 B2 | 9/2017 | Mckinney et al. |
| 2005/0037412 A1 | 2/2005 | Meier et al. |
| 2011/0027833 A1 | 2/2011 | Hogrefe et al. |
| 2011/0281305 A1 | 11/2011 | Bourn et al. |
| 2013/0034879 A1 | 2/2013 | Skirgaila et al. |
| 2013/0040365 A1 | 2/2013 | Vander Horn et al. |
| 2013/0252309 A1 | 9/2013 | Kermekchiev et al. |
| 2014/0113299 A1 | 4/2014 | Kermekchiev et al. |
| 2015/0166968 A1 | 6/2015 | Wang et al. |
| 2015/0368626 A1 | 12/2015 | Vander Horn et al. |
| 2017/0096648 A1 | 4/2017 | Mazur et al. |
| 2018/0230462 A1 | 8/2018 | Gong et al. |

OTHER PUBLICATIONS

NCBI Reference Sequence WP_018461567.1, published Jun. 28, 2013 (Year: 2013).*

NCBI Reference Sequence WP_027881614.1, published Jun. 12, 2014 (Year: 2014).*

NCBI Reference Sequence WP_071676319.1, published Nov. 18, 2016 (Year: 2016).*

Geneseq Accession No. ARQ00527, published Jul. 10, 2008 (Year: 2008).*

Geneseq Accession No. BAK47842, published Apr. 11, 2013 (Year: 2013).*

International Search Report and Written Opinion from PCT/US2019/013673 dated May 23, 2019; 12 pages.

Guilliam, T.A. et al.; "Molecular Basis for PrimPol Recruitment to Replication Forks by RPA"; *Nature Communications*; vol. 8; May 23, 2017; pp. 1-14.

Baar, Claudia et al. "Molecular breeding of polymerases for resistance to environmental inhibitors," Published: Feb. 4, 2011, Nucleic Acids Research, vol. 39, No. 8, pp. 1-12.

Life Technologies Corporation. Real-time PCR handbook, 2012, pp. 1-70.

* cited by examiner

FIG. 1

```
SEQ_ID_NO1         ---MLPLFEPKGRVLLVDGHHLAYRNFFTLKGPTTSRGEPVQGVYGFAKSLAKALKEDGD  57
SEQ_ID_NO2         ---MLPLFEPKGRVLLVDGHHLAYRNFFTLKGLTTSRGEPVQGVYGFAKSLAKALKEDGD  57
SEQ_ID_NO3         ---MLPLFEPKGRVLLVDGHHLAYRNFFTLRGLTTSRGEPVQGVYGFAKSLAKALKEDGD  57
SEQ_ID_NO4         ---MLPLFEPKGRVLLVDGHHLAYRNFFTLKGPTTSRGEPVQGVYGFAKSLAKALKEDGD  57
SEQ_ID_NO5         ---MLPLFEPKGRVLLVDGHHLAYRNFFTLKGLTTSRGEPVQGVYGFAKSLAKALKEDGD  57
SEQ_ID_NO6         ---MLPLFEPKGRVLLVDGHHLAHRNFFALKGLTTSRGEPVQGVYGFAKSLLKALKEDGD  57
SEQ_ID_NO7         ---MLPLFEPKGRVLLVDGHHLAYRTFFALKGLTTSRGEPVQGVYGFAKSLLKALKEDGE  57
SEQ_ID_NO8 (Taq)   MRGMLPLFEPKGRVLLVDGHHLAYRTFHALKGLTTSRGEPVQAVYGFAKSLLKALKEDGD  60
                      ********************* **  ***** ********* ***********:

SEQ_ID_NO1         VVIVVFDAKAPSFRHEAYGAYKAGRAPTPEDFPRQLALMKELVDLLGLERLEVPGFEADD 117
SEQ_ID_NO2         VVIVVFDAEAPSFRHEAYGAYKAGRAPTREDFPRQLALMKELVDLLGLERLEVPGFEADD 117
SEQ_ID_NO3         VVIVVFDAKAPSFRHEAYGAYKAGRAPTPEDFPRQLALMKELVDLLGLERLEVPGFEADD 117
SEQ_ID_NO4         VVIVVFDAKAPSFRHETYGAYKAGRAPTPEDFPRQLALMKELVDLLGLERLEVPGFEADD 117
SEQ_ID_NO5         VVIVVFDAKAPSFRHEAYGAYKAGRAPTPEDFPRQLALMKELVDLLGLERLEVPGFEADD 117
SEQ_ID_NO6         VVIVVFDAKAPSFRHEAYGAYEAGRAPTPEDFPRQLALIKELVDLLGLVRLEVPGFEADD 117
SEQ_ID_NO7         VAIVVFDAKAPSFRHEAYEAYKAGRAPTPEDFPRQLALIKELVDLLGLVRLEVPGFEADD 117
SEQ_ID_NO8 (Taq)   AVIVVFDAKAPSFRHEAYGGYKAGRAPTPEDFPRQLALIKELVDLLGLARLEVPGYEADD 120
                    .:********** :  .***.********:***********::*********:****

SEQ_ID_NO1         VLAALAKIAEREGYEVRILTADRDLFQLLSDRIALLHPEGHLITPGWLWERYGLRPEQWV 177
SEQ_ID_NO2         VLAALAKIAEREGYEVRILTADRDLFQLLSDRIAVLHPEGHLITPGWLWERYGLRPEQWV 177
SEQ_ID_NO3         VLAALAKIAEREGYEVRILTADRDLFQLLSDRIAVLHPEGHLITPGWLWERYGLRPEQWV 177
SEQ_ID_NO4         VLAALAKIAEREGYEVRILTADRDLFQLLSDRIAVLHPEGHLITPGWLWERYGLRPEQWV 177
SEQ_ID_NO5         VLAALAKIAEREGYEVRILTADKDLYQILSDRIAVLHPEGHLITPGWLWERYGLRPEQWV 177
SEQ_ID_NO6         VLATLAKKAEKEGYEVRILTADKDLYQLLSDRVHVLHPEGYLITPAWLWEKYGLRPEQWV 177
SEQ_ID_NO7         VLAALAKKAEREGYEVRILSADRDLYQLLSDRIHLLHPEGYLITPAWLWEKYGLRPDQWA 177
SEQ_ID_NO8 (Taq)   VLASLAKKAEKEGYEVRILTADKDLYQLLSDRIHVLHPEGYLITPAWLWEKYGLRPDQWA 180
                   *** *** ** **********:** **:*:****::.****:****.****:*****:*:
```

FIG. 1 (continued)

```
SEQ_ID_NO1       DFRALAGDPSDNIPGVKGISEKTALKLLKEWGSLENIQKNLAQVKPERVREAIRNNLDKL 237
SEQ_ID_NO2       DFRALAGDPSDNIPGVKGISEKTALKLLKEWGSLENIQKNLAQVKPERVREAIRNNLDKL 237
SEQ_ID_NO3       DFRALTGDPSDNIPGVKGIGEKTALKLLKEWGSLENIQKNLDQVKPERVREAIRNNLDKL 237
SEQ_ID_NO4       DFRALAGDPSDNIPGVKGIGEKTALKLLKEWGSLENIQKNLDQVKPERVREAIRNNLDKL 237
SEQ_ID_NO5       NFRALAGDPSDNIPGVKGIGEKTALKLLKEWGSLENIQKNLDQVKPERVREAIRNNLDKL 237
SEQ_ID_NO6       DYRALTGDESDNLPGVKGIGEKTARKLLEEWGSLEALLKNLDRLKPA-IREKILAHMDDL 236
SEQ_ID_NO7       DYRALTGDESDNLPGVKGIGEKTARKLLEEWGSLEALLKNLDRLKPA-IREKILAHMDDL 236
SEQ_ID_NO8(Taq)  DYRALTGDESDNLPGVKGIGEKTARKLLEEWGSLEALLKNLDRLKPA-IREKILAHMDDL 239
                 ::***:**.**:******.******:***** :** ::**:****  ***:******

SEQ_ID_NO1       QMSLELSRLRTDLPLEVDFRRRREPDREGLRAFLERLEFGSLLHEFGLLESPKALEEEALW 297
SEQ_ID_NO2       QMSLELSRLRTDLPLEVDFRRRREPDREGLRAFLERLEFDSLLHEFGLLESPKALEEEALW 297
SEQ_ID_NO3       QMSLELSRLRTDLPLEVDFRRRREPDREGLRAFMERLEFGSLLHEFGLLESPKALEEEALW 297
SEQ_ID_NO4       QMSLELSRLRTDLPLEVDFRRRREPDREGLRAFLERLEFGSLLHEFGLLESPKALEEEALW 297
SEQ_ID_NO5       QMSLELSCLRTDLPLEVDFRRRREPDREGLRAFLERLEFGSLLHEFGLLESPKALEEEALW 297
SEQ_ID_NO6       KLSWDPAKVRTDLPLEVDFAKRREPDRERLRAFLERLEFGSLLHEFGLLESPKALEEEALW 296
SEQ_ID_NO7       KLSWDPAKVRTDLPLEVDFAKRREPDRERLRAFLERLEFGSLLHEFGLLESPKALEEEAPW 296
SEQ_ID_NO8(Taq)  KLSWDLAKVRTDLPLEVDFAKRREPDRERLRAFLERLEFGSLLHEFGLLESPKALEEEAPW 299
                 ::*  :******:*****.::****:.*****:*****.************:*****.*

SEQ_ID_NO1       PPPEGAFVGFVLSRKEPMWADLLALAAARGGRVHRAPEPYKALRDLKEARGLLAKDLSVL 357
SEQ_ID_NO2       PPPEGAFVGFVLSRKEPMWADLLALAAARGGRVHRAPEPYKALRDLKEARGLLAKDLSVL 357
SEQ_ID_NO3       PPPEGAFVGFVLSRKEPMWADLLALAAARGGRVHRAPEPYKALRDLKEARGLLAKDLSVL 357
SEQ_ID_NO4       PPPEGAFVGFVLSRKEPMWADLLALAAARGGRVHRAPEPYKALRDLKEARGLLAKDLSVL 357
SEQ_ID_NO5       PPPEGAFVGFVLSRKEPMWADLLALAAARGGRVHRAPEPYKALRDLKEARGLLAKDLSVL 357
SEQ_ID_NO6       PPPEGAFVGFVLSRKEPMWADLLALAAARGGRVHRAPEPYKALRDLKEARGLLAKDLSVL 356
SEQ_ID_NO7       PPPEGAFVGFVLSRKEPMWADLLALAAARGGRVHRAPEPYKALRDLKEARGLLAKDLSVL 356
SEQ_ID_NO8(Taq)  PPPEGAFVGFVLSRKEPMWADLLALAAARGGRVHRAPEPYKALRDLKEARGLLAKDLSVL 359
                 ************************************************************
```

FIG. 1 (continued)

```
SEQ_ID_NO1        ALREGLGLPPGDDPMLLAYLLDPSNTTPEGVARRYGGEWTEEAGERAALSERLFADLWGR 417
SEQ_ID_NO2        ALREGLGLPPGDDPMLLAYLLDPSNTTPEGVARRYGGEWTEEAGERAALSERLFADLWGR 417
SEQ_ID_NO3        ALREGLGLPPGDDPMLLAYLLDPSNTTPEGVARRYGGEWTEEAGERAALSERLFANLWSR 417
SEQ_ID_NO4        ALREGLGLPPGDDPMLLAYLLDPSNTTPEGVARRYGGEWTEEAGERAALSERLFANLWGR 417
SEQ_ID_NO5        ALREGLGLPPGDDPMLLAYLLDPSNTTPEGVARRYGGEWTEEAGERAALSERLFANLWGR 417
SEQ_ID_NO6        ALREGLGLPPGDDPMLLAYLLDPSNTTPEGVARRYGGEWTEEAGERAALSERLFADLWGR 416
SEQ_ID_NO7        ALREGLGLPPGDDPMLLAYLLDPSNTTPEGVARRYGGEWTEEAGERAALSERLFANLWGR 416
SEQ_ID_NO8 (Taq)  ALREGLGLPPGDDPMLLAYLLDPSNTTPEGVARRYGGEWTEEAGERAALSERLFANLWGR 419
                  ************************************************:*.:. *

SEQ_ID_NO1        LEGEERLLWLYREVERPLSAVLAHMEATGVRLDVAYLRALSLEVAEEIARLEAEVFRLAG 477
SEQ_ID_NO2        LEEEERLLWLYHEVERPLSAVLAHMEATGVRLDVAYLRALSLEVAEEIARLEAEVFRLAG 477
SEQ_ID_NO3        LEGEERLLWLYREVERPLSVVLAHMEATGVRLDVAYLRALSLEVAEEIARLEAEVFRLAG 477
SEQ_ID_NO4        LEGEERLLWLYREVERPLSAVLAHMEATGVRLDVAYLRALSLEVAEEIARLEAEVFRLAG 477
SEQ_ID_NO5        LEGEERLLWLYREVERPLSAVLARMEATGVRLDVAYLRALSLEVAEEIARLEAEVFRLAG 477
SEQ_ID_NO6        LEGEERLLWLYREVERPLSAVLAHMEATGVRLDVAYLRALSLEVAEEIARLEAEVFRLAG 476
SEQ_ID_NO7        LEGEERLLWLYREVERPLSAVLAHMEATGVRLDVAYLRALSLEVAEEIARLEAEVFRLAG 476
SEQ_ID_NO8 (Taq)  LEGEERLLWLYREVERPLSAVLAHMEATGVRLDVAYLRALSLEVAEEIARLEAEVFRLAG 479
                  ** *********:******:***.*************************************

SEQ_ID_NO1        HPFNLNSRDQLERVLFDELGLPAIGKTEKTGKRSTSAAVLEALREAHPIVEKILQYRELT 537
SEQ_ID_NO2        HPFNLNSRDQLERVLFDELGLPAIGKTEKTGKRSTSAAVLEALREAHPIVEKILQYRELA 537
SEQ_ID_NO3        HPFNLNSRDQLERVLFDELGLPPIGKTEKTGKRSTSAAVLEALREAHPIVEKILQYRELA 537
SEQ_ID_NO4        HPFNLNSRDQLERVLFDELGLPPIGKTEKTGKRSTSAAVLEALREAHPIVEKILQYRELA 537
SEQ_ID_NO5        HPFNLNSRDQLERVLFDELGLPPIGRTEKTGKRSTSAAVLEALREAHPIVEKILQYRELA 537
SEQ_ID_NO6        HPFNLNSRDQLERVLFDELGLPAIGKTEKTGKRSTSAAVLEALREAHPIVEKILQYRELT 536
SEQ_ID_NO7        HPFNLNSRDQLERVLFDELGLPAIGKTEKTGKRSTSAAVLEALREAHPIVEKILQYRELT 536
SEQ_ID_NO8 (Taq)  HPFNLNSRDQLERVLFDELGLPAIGKTEKTGKRSTSAAVLEALREAHPIVEKILQYRELT 539
                  *********************:** *************************************:
```

FIG. 1 (continued)

```
SEQ_ID_NO1        KLKSTYIDPLPRLVHPKTGRLHTRFNQTATATGRLSSSDPNLQNIPVRTPLGQRIRRAFI 597
SEQ_ID_NO2        KLKSTYIDPLPRLVHPKTGRLHTRFNQTATATGRLSSSDPNLQNIPVRTPLGQRIRKAFI 597
SEQ_ID_NO3        KLKSTYIDPLPRLVHPKTGRLHTRFNQTATATGRLSSSDPNLQNIPVRTPLGQRIRKAFI 597
SEQ_ID_NO4        KLKSTYIDPLPRLVHPKTGRLHTRFNQTATATGRLSSSDPNLQNIPVRTPLGQRIRKAFI 597
SEQ_ID_NO5        KLKSTYIDPLPRLVHPKTGRLHTRFNQTATATGRLSSSDPNLQNIPVRTPLGQRIRKAFI 597
SEQ_ID_NO6        KLKSTYIDPLPRLVHPKTGRLHTRFNQTATATGRLSSSDPNLQNIPVRTPLGQRIRKAFI 596
SEQ_ID_NO7        KLKSTYIDPLPRLVHPKTGRLHTRFNQTATATGRLSSSDPNLQNIPVRTPLGQRIRRAFI 596
SEQ ID NO8 (Taq)  KLKSTYIDPLPDLIHPRTGRLHTRFNQTATATGRLSSSDPNLQNIPVRTPLGQRIRRAFI 599
                  ***********  *:***:*****************************:***:****

SEQ_ID_NO1        AEEGWLLVALDYSQIELRVLAHLSGDENLIRVFQEGRDIHTETASWMFGVPREAVDPLMR 657
SEQ_ID_NO2        AEEGWLLVALDYSQIELRVLAHLSGDENLIRVFREGKDIHTETASWMFGVPREAVDPLMR 657
SEQ_ID_NO3        AEEGWLLVALDYSQIELRVLAHLSGDENLIRVFREGKDIHTETASWMFGVPREAVDPLMR 657
SEQ_ID_NO4        AEEGWLLVALDYSQIELRVLAHLSGDENLIRVFREGKDIHTETAAWMFGVPREAVDPLMR 657
SEQ_ID_NO5        AEEGWLLVALDYSQIELRVLAHLSGDENLIRVFREGKDIHTETASWMFGVPPEGVDPLMR 657
SEQ_ID_NO6        AEEGHLLVALDYSQIELRVLAHLSGDENLIRVFQEGKDIHTETAAWMFGVPPEGVDGAMR 656
SEQ_ID_NO7        AEEGWLLVALDYSQIELRVLAHLSGDENLIRVFQEGRDIHTETASWMFGVPREAVDPLMR 656
SEQ ID NO8 (Taq)  AEEGWLLVALDYSQIELRVLAHLSGDENLIRVFQEGRDIHTETASWMFGVPREAVDPLMR 659
                  ****:************************** **:*********:****** *.*  **

SEQ_ID_NO1        RAAKTINFGVLYGMSAHRLSQELAIPYEEAQAFIERYFQSFPKVRAWIAHTLEEGRKKGY 717
SEQ_ID_NO2        RAAKTINFGVLYGMSAHRLSQELSIPYEEAAAFIERYFQRFPQVRAWIAHTLEEGRKKGY 717
SEQ_ID_NO3        RAAKTINFGVLYGMSAHRLSQELSIPYEEAAAFIERYFQRFPQVRAWIEKTLEEGRQRGY 717
SEQ_ID_NO4        RAAKTVNFGVLYGMSAHRLSQELSIPYEEAAAFIERYFQRFPQVRAWIAHTLEEGRKKGY 717
SEQ_ID_NO5        RAAKTINFGVLYGMSAHRLSQELSIPYEEAVAFIERYFQSFPQVRAWIAHTLEEGRKKGY 717
SEQ_ID_NO6        RAAKTVNFGVLYGMSAHRLSQELSIPYEEAAAFIERYFQSFPQVRAWIAHTLEEGRKKGY 716
SEQ_ID_NO7        RAAKTINFGVLYGMSAHRLSQELAIPYEEAQAFIERYFQSFPKVRAWIERTLEEGRQRGY 716
SEQ ID NO8 (Taq)  RAAKTINFGVLYGMSAHRLSQELAIPYEEAQAFIERYFQSFPKVRAWIEKTLEEGRRRGY 719
                  *****:****************:*******.********.**:**** :****: :**
```

FIG. 1 (continued)

```
SEQ_ID_NO1       VETLFGRRRYVPDLNARVKSVREAAERMAFNMAVQGTAADLMKLAMVKLFPRLPEVGARM 777
SEQ_ID_NO2       VETLFGRRRYVPDLNARVKSVREAAERMAFNMAVQGTAADLMKLAMVKLFPRLRPLGVRM 777
SEQ_ID_NO3       VETLFGRRRYVPDLNARVKRVREAAERMAFNMPVQGTAADLMKLAMVRLFPRLPEVGARM 777
SEQ_ID_NO4       VETLFGRRRYVPDLNARVKSVREAAERMAFNMAVQGTAADLMKLAMVKLFPRLPEVGARM 777
SEQ_ID_NO5       VETLFGRRRYVPDLNARVKSVREAAERMAFNMAVQGTAADLMKLAMVKLFPRLPEVGARM 777
SEQ_ID_NO6       VETLFGRRRYVPDLNARVKSVRKAAERMAFNMAVQGTAADLMKLAMVKLFPRLPEVGARM 776
SEQ_ID_NO7       VETLFGRRRYVPDLNARVKRVRKAAERMAFNMPVQGTAADLMKLAMVRLFPRLPEVGARM 776
SEQ_ID_NO8 (Taq) VETLFGRRRYVPDLEARVKSVREAAERMAFNMPVQGTAADLMKLAMVKLFPRLEEMGARM 779
                 *************:*****:*.*****************:*******:****.:*.**

SEQ_ID_NO1       LLQVHDELLLEAPKERAEEAAALAKEVMEGVWPLAVPLEVEVGIGEDWLSAKG 830
SEQ_ID_NO2       LLQVHDELLLEAPKERAEEAAALAKEVMEGVWPLAVPLEVEVGIGEDWLSAKG 830
SEQ_ID_NO3       LLQVHDELLLEAPKERAEEAAALAREVMEGVWPLAVPLEVEVGIGEDWLSAKG 830
SEQ_ID_NO4       LLQVHDELLLEAPKERAEEAAALAKEVMEGVWPLAVPLEVEVGIGEDWLSAKG 830
SEQ_ID_NO5       LLQVHDELLLEAPKERAEEAAALAKEVMEGVWPLAVPLEVEVGIGEDWLSAKG 830
SEQ_ID_NO6       LLQVHDELLLEAPKERAEEAAALAKEVMEGVWPLAVPLEVEVGIGEDWLSAKG 830
SEQ_ID_NO7       LLQVHDELLLEAPKERAEEAAQLAKETMEGVWPLAVPLEVEVGIGEDWLSAKE 829
SEQ_ID_NO8 (Taq) LLQVHDELVLEAPKERAEAVARLAKEVMEGVYPLAVPLEVEVGIGEDWLSAKE 832
                 ********:.*******.  *. **:.***** *******************
```

MUTANT DNA POLYMERASES

CROSS-REFERENCES TO RELATED APPLICATIONS

This application claims the benefit of U.S. Provisional Application 62/619,394 filed on Jan. 19, 2018 which is hereby incorporated by reference in its entirety.

REFERENCE TO SUBMISSION OF A SEQUENCE LISTING AS A TEXT FILE

The Sequence Listing written in file 094260-1116787_115810US_SL.txt created on Dec. 16, 2018, 82,590 bytes, machine format IBM-PC, MS-Windows operating system, is hereby incorporated by reference in its entirety for all purposes.

BACKGROUND

The detection, analysis, transcription, and amplification of nucleic acids are frequently-used procedures in modern molecular biology. Polymerase chain reaction (PCR) is an example of such a commonly used method. PCR is used to study gene expression and in the diagnosis of infectious or genetic diseases, to name but a few applications.

A component of PCR is DNA polymerase, which synthesizes new DNA complimentary to a segment of DNA. A variety of thermostable polymerases have been discovered. At least five families of DNA-dependent DNA polymerases are known, although most fall into families or types A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerization and 3' to 5' exonuclease activity.

Of the many different polymerases commercially available, Taq DNA polymerase (a Type-A DNA polymerase) is a popular choice because it is thermostable, efficient and easy to produce. The enzymatic activity of Taq DNA polymerase, however, can be reduced due to endogenous polymerase inhibitors present in the sample being tested or due to inhibiting substances that have been added to the sample (e.g., anticoagulant added to a blood sample).

SUMMARY

Provided herein is a mutant Type-A DNA polymerase comprising mutations corresponding to one or more amino acid residues 551, 788, and 798 of a wild-type *Thermus aquaticus* (Taq) DNA polymerase. The mutant polymerase possesses a higher resistance to a polymerization activity inhibitor than the wild-type DNA polymerase. In some embodiments, the mutant Type-A DNA polymerase comprises mutations at D551R, V788L, and A798E. In some embodiments, the mutant Type-A DNA polymerase comprises one or more additional mutations at amino acid residues selected from the group consisting of 52, 99, 109, 128, 154, 259, 268, and 739. In certain embodiments, the mutant Type-A DNA polymerase comprises mutations at L52A, I99M, A109E, K128I, H154A, A259R, R268G, and S739R. In some embodiments, the mutant Type-A DNA polymerase has at least 85% identity (or at least 90%, 91%, 92%, 93%, 94%, 95%, 96%, 97%, 98%, 99% identity) to an amino acid sequence selected from the group consisting of SEQ ID NOs: 1, 2, 3, 4, 5, 6, and 7. In some embodiments, the mutant Type-A DNA polymerase comprises SEQ ID NO: 1, SEQ ID NO: 2, SEQ ID NO: 3, SEQ ID NO: 4, SEQ ID NO: 5, SEQ ID NO: 6, or SEQ ID NO: 7. In some embodiments, the mutant Type-A DNA polymerase is thermostable at 98° C. for at least 15 minutes.

In some embodiments, the polymerization activity inhibitor is from a blood sample. In some embodiments, the polymerization activity inhibitor is an anticoagulant. In certain embodiments, the polymerization activity inhibitor is heparin.

Also provided is a composition comprising (i) the mutant Type-A DNA polymerase as described above or elsewhere herein and (ii) one or more reagents selected from the group consisting of an aqueous buffer, a metal ion, nucleotides, primers, probes, a detergent, a dye, a detection agent, and a target nucleic acid.

Also provided is a method of amplifying a target nucleic acid. In some embodiments, the method comprises contacting a test sample suspected of containing the target nucleic acid with a mutant polymerase as described above or elsewhere herein, at least one primer that specifically binds to the target nucleic acid, and nucleotides to form a mixture; and incubating the mixture under conditions permitting extension of the at least one primer by the polymerase using the sequence of the target nucleic acid as a template for incorporation of the nucleotides. In some embodiments, the method is PCR. In some embodiments, the method is qPCR, reverse transcription PCR (RT-PCR), or ddPCR. In certain embodiments, the conditions include the presence of an inhibitor of the wild-type DNA polymerase at a concentration that is inhibitory to the wild-type DNA polymerase. In some embodiments, the test sample is a blood sample or a fraction of blood.

Also provided is a nucleic acid comprising a nucleotide sequence that encodes the mutant thermostable Type-A DNA polymerase described above or elsewhere herein. Also provided is a vector comprising the nucleic acid described above or elsewhere herein. Also provided is a host cell comprising the vector described above or elsewhere herein.

Also provided is a method of producing a polypeptide. In some embodiments, the method comprises culturing a host cell comprising a nucleic acid comprising a nucleotide sequence that encodes the mutant thermostable Type-A DNA polymerase described above or elsewhere herein in a medium under conditions permitting expression of a polypeptide encoded by the nucleic acid; and purifying the polypeptide from the cultured cell or medium.

Also provided is a kit for amplifying a target nucleic acid. In some embodiments, the kit comprises (i) the mutant thermostable Type-A DNA polymerase described above or elsewhere herein and (ii) one or more reagents selected from the group consisting of an aqueous buffer, a metal ion, nucleotides, primers, probes, a detergent, a detection agent, a dye, an anticoagulant, and a cell lysis agent.

BRIEF DESCRIPTION OF THE DRAWINGS

FIG. 1 shows an alignment of an exemplary Type-A DNA polymerase (i.e., Taq polymerase, SEQ ID NO: 8) and mutant Type-A DNA polymerases (SEQ ID NOS: 1-7).

DETAILED DESCRIPTION

Described herein are mutant Type-A DNA polymerases that are more resistant to inhibitors of DNA polymerase activity. The genetically engineered or mutant DNA polymerases are suitable for use in nucleic acid amplification methods, e.g., PCR, quantitative PCR (qPCR), reverse transcription PCR (RT-PCR), or digital droplet PCR (ddPCR).

I. DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Green et al., MOLECULAR CLONING, A LABORATORY MANUAL (FOURTH EDITION), Cold Spring Harbor Laboratory Press (Cold Spring Harbor, N.Y. 2012).

The term "amplification composition" or "amplification reaction mixture" refers to an aqueous solution comprising the various reagents used to amplify a target nucleic acid. These include enzymes, aqueous buffers, salts, amplification primers, target nucleic acid, and nucleoside triphosphates. As discussed further herein, amplification composition may also further include stabilizers and other additives to optimize efficiency and specificity. Depending upon the context, the mixture can be either a complete or incomplete amplification composition.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "template" refers to a polynucleotide sequence that comprises the polynucleotide to be amplified, flanked by primer hybridization sites. Thus, a "target template" comprises the target polynucleotide sequence flanked by hybridization sites for a 5' primer and a 3' primer.

As used herein, "nucleic acid" means DNA, RNA (single-stranded or double-stranded), and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "nucleic acid", "oligonucleotide" or "polynucleotide" interchangeably refer to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™), and the like. In certain applications, the nucleic acid can be a polymer that includes multiple monomer types, e.g., both RNA and DNA subunits.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid. Any of the polynucleotides described herein can be included in a vector.

A "DNA polymerase" or a "polymerase," as used herein, refers to an enzyme that performs template-directed synthesis of DNA. The term encompasses both the full length polypeptide and a domain that has polymerase activity. DNA polymerases are well-known to those skilled in the art, including but not limited to DNA polymerases isolated or derived from *Pyrococcus furiosus*, *Thermococcus litoralis*, *Bacillus stearothermophilus*, and *Thermotoga* maritime, or modified versions thereof.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region or the entire designated sequence if a region is not specified), when compared and aligned for maximum correspondence over a comparison window.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

Percent sequence identity and sequence similarity can be determined using the BLAST 2.0 algorithm, which is described in Altschul et al. (J. Mol. Biol. 215:403-10, 1990). Software for performing BLAST 2.0 analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

As used in this specification and the appended claims, the singular forms "a", "an", and "the" include plural referents unless the content clearly dictates otherwise. As used herein, the term "about" refers to the recited number and any value within 10% of the recited number. Thus, "about 5" refers to any value between 4.5 and 5.5, including 4.5 and 5.5.

II. POLYMERASES

In an embodiment, a mutant Type-A DNA polymerase comprises at least three mutations corresponding to (or aligning with) one or more amino acid residues 551, 788, and 798 of a wild-type *Thermus aquaticus* (Taq) DNA polymerase. The mutant polymerase possesses a higher resistance to a polymerization activity inhibitor than the wild-type DNA polymerase, i.e., acceptable levels of DNA polymerization or correct amplification of a desired product occurs in the presence of one or more inhibitors. As used herein, the mutant DNA polymerase is resistant to inhibition if it has a delta delta quantitation cycle value (or delta delta Cq value) obtained by quantitative PCR that is about 0.5 or more. In some embodiments, the delta delta Cq value of the mutant is about 1 to about 5. In some embodiments, the delta delta Cq value of the mutant is at least about 5. As used herein, the Cq value is the quantitation cycle value at which the (baseline-corrected) amplification curve (i.e., relative fluorescence units plotted as a function of number of cycles) crosses an arbitrary threshold value. The delta Cq value is defined as:

$$\text{Delta Cq value} = \text{Cq value}_{presence} - \text{Cq value}_{absence} \quad (1)$$

where Cq value$_{presence}$ is the Cq value in the presence of inhibitor and Cq value$_{absence}$ is the Cq value in the absence of inhibitor.
The delta delta Cq value$_{mutant}$ is defined as:

$$\text{Delta delta Cq value}_{mutant} = \text{delta Cq value}_{reference} - \text{delta Cq value}_{mutant} \quad (2)$$

where delta Cq value$_{reference}$ is the delta Cq value of a reference Type-A DNA polymerase and delta Cq value$_{mutant}$ is the delta Cq value of the mutant. In some embodiments, the reference Type-A DNA polymerase is wild type Taq polymerase. In certain embodiments, the reference Type-A DNA polymerase is a non-wild type Taq polymerase. In either case, the reference polymerase is otherwise identical to the mutant polymerase except that the reference will have the wildtype amino acid at the mutant positions (e.g., including but not necessarily limited to D551, V788, and A798).

In some embodiments, the mutant Type-A DNA polymerase comprises one or more additional mutations at amino acid residues 52, 99, 109, 128, 154, 259, 268, and 739. FIG. 1 lists seven examples of such mutant Type-A DNA polymerases (SEQ ID NOS: 1-7) as compared to wild-type Taq DNA polymerase (SEQ ID NO: 8). Mutations corresponding to amino acid residues 52, 99, 109, 128, 154, 259, 268, 551, 739, 788, and/or 798 of wild-type Taq DNA polymerase can be located in FIG. 1. The position designations do not indicate the numeric position of the amino acid in question and instead refers to where a maximally aligned amino acid occurs in a wild-type Taq DNA polymerase.

In some embodiments, the mutant Taq DNA polymerases comprise mutations at D551R, V788L, and A798E. In some embodiments, the mutant Type-A DNA polymerase comprises one or more additional mutations at L52A, I99M, A109E, K128I, H154A, A259R, R268G, and/or S739R. In certain embodiments, the mutant Type-A DNA polymerase comprises SEQ ID NO: 1, SEQ ID NO: 2, SEQ ID NO: 3, SEQ ID NO: 4, SEQ ID NO: 5, SEQ ID NO: 6, or SEQ ID NO: 7. Table 1 below lists the amino acid positions and the corresponding mutations in seven exemplary mutant Type-A DNA polymerases (i.e., for SEQ ID NOS: 1-7).

TABLE 1

| Position | Mutation | SEQ ID #1 | SEQ ID #2 | SEQ ID #3 | SEQ ID #4 | SEQ ID #5 | SEQ ID #6 | SEQ ID #7 |
|---|---|---|---|---|---|---|---|---|
| 1 L52 | A | x | x | x | x | x | | |
| 2 I99 | M | x | x | x | x | x | | |
| 3 A109 | E | x | x | x | x | x | | |
| 4 K128 | I | x | x | x | x | x | | |
| 5 H154 | A | x | x | x | x | x | | |
| 6 A259 | R | x | x | x | x | x | | |
| 7 R268 | G | x | x | x | x | x | | |
| 8 D551 | R | x | x | x | x | x | x | x |
| 9 S739 | R | | | x | | | | x |
| 10 V788 | L | x | x | x | x | x | x | x |
| 11 A798 | E | x | x | x | x | x | x | x |

The mutant Type-A DNA polymerases are resistant to inhibitors found in blood samples including, but not limited to lactoferrin, immunoglobulin G (IgG), plasma, and proteases. In some embodiments, the mutant Type-A DNA polymerases are resistant to anticoagulants in blood samples, e.g., heparin. Resistance to inhibitors found in blood samples, including inhibitors such as anticoagulants that are added to blood, is germane to medical and forensic analysis.

In some embodiments, the mutant Type-A DNA polymerases are more thermostable than wild-type Type-A DNA polymerase. As used herein, thermostable refers to a polymerase in which there is no change (i.e., increase) in Cq value as measured by qPCR before and after being incubated at a given temperature and incubation time (i.e., delta Cq=Cq after heat treatment–Cq before heat treatment=0). In some embodiments, the mutant Type-A DNA polymerases are thermostable at 94° C. or higher for at least 15 seconds. In some embodiments, the mutant Type-A DNA polymerases are thermostable at 98° C. for at least 15 minutes.

The mutant DNA polymerases described in the Examples are mutant forms of wild-type Taq DNA polymerase, which have altered features that provide the mutant polymerases with improved inhibitor resistance. However, it is to be understood that the mutant polymerases are not limited to the exemplary embodiments discussed herein. For example, mutants of polymerases other than Taq DNA polymerase, e.g., mutants of any Type-A family DNA polymerase are included. These mutants can be mutants of the polymerases including, but not limited to, those from the genus *Thermus*. Type-A DNA polymerases show high levels of sequence identity and conservation and one can identify residues of one particular Type-A DNA polymerase that correspond to residues of another. Thus, reference herein to specific mutations in wild-type Taq DNA polymerase can be correlated to corresponding mutations in other polymerases.

FIG. 1 shows an alignment of the primary amino acid sequences of wild-type Type-A Taq DNA polymerase from *Thermus aquaticus* with the mutant Type-A DNA polymerases SEQ ID NOS: 1-7. As shown in FIG. 1, various regions of the wild-type and mutant Type-A DNA polymerases are highly conserved while other regions are variable. Mutations in addition to those specifically identified and discussed herein may be made in the variable regions of Type-A DNA polymerases without altering, or without substantially altering, the polymerase activity of the mutated enzyme. Likewise, conservative mutations at conserved residues may be made without altering, or substantially altering, the polymerase activity of the mutated enzyme. Using the structural data and known physical properties of amino acids, those of skill in the art can mutate enzymes, such as the DNA polymerases described herein, without altering, or without substantially altering, the essential enzymatic characteristics of the enzymes.

The amino acid sequence of the mutant DNA polymerase polypeptides described herein may vary without disrupting the ability to catalyze the replication of DNA under primer extension reaction conditions and/or PCR reaction conditions as described herein in the presence of inhibitors in samples. For example, the mutants can contain one or more (e.g., 1-10) conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), (3-branched side chains (e.g., threonine, valine, isoleucine) and aromatic side chains (e.g., tyrosine, phenylalanine, tryptophan, histidine). Thus, a predicted nonessential amino acid residue in the SEQ ID NOS: 1-7 can be replaced with another amino acid residue from the same side chain family. Mutations can be introduced randomly along all or part of the sequences by processes including, but not limited to, site directed mutagenesis, gene-shuffling, and/or directed evolution.

Also provided is a variant of a polypeptide or a polypeptide derivative of each of the mutants, e.g., a protein having one or more point mutations, insertions, deletions, truncations, a fusion protein, or a combination thereof. The functional equivalent substantially retains the activity of the mutant DNA polymerases under PCR conditions described herein (e.g., a PCR reaction mixture containing a blood sample that contains a polymerase inhibitor and accounts for at least 1% (e.g., 2%, 2.5%, 5%, 10%, 20%, 25%, 30%, 35%, 40%, 45%, or 50%) v/v of the mixture). In some embodiments, the isolated polypeptide can contain any one of SEQ ID NOS: 1-7 or a functional fragment or equivalent thereof. In general, the functional equivalent is at least 70% (e.g., any number between 70% and 100%, inclusive, e.g., 70%, 75%, 80%, 85%, 90%, 91%, 92%, 93%, 94%, 95%, 96%, 97%, 98%, and 99%) identical to any one of SEQ ID NOS: 1-7, respectively.

A polypeptide as described herein can be a recombinant polypeptide. To prepare a recombinant polypeptide, a nucleic acid encoding it can be linked to another nucleic acid encoding a fusion partner, e.g., glutathione-s-transferase (GST), 6×-His epitope tag (SEQ ID NO:16), or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide as described herein. Alternatively, the polypeptides can be chemically synthesized (see e.g., Creighton, "Proteins: Structures and Molecular Principles," W.H. Freeman & Co., NY, 1983), or produced by recombinant DNA technology as described herein.

The mutant DNA polymerases described herein can be provided in purified or isolated form, or can be part of a composition. When in a composition, the mutant DNA polymerases are first purified to a purity of about 80%, 90%, 95%, or 99% or more. The mutant polymerases can be purified by standard procedures in the art, e.g., by ammonium sulfate precipitation, chromatography, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)). Compositions as described herein can be any type of composition desired, but typically are aqueous compositions suitable for use in the amplification of a target nucleic acid, e.g., through use of a PCR technique. As such, the compositions typically comprise at least one substance other than the mutant DNA polymerase, e.g., water, glycerol or another stabilizing agent, an aqueous buffer, an aqueous salt buffer, a metal ion, (e.g, a divalent metal such as magnesium). In exemplary embodiments, the compositions comprise some or all of the solvents, salts, buffers, nucleotides, and other reagents typically present in a PCR reaction. Thus, in some embodiments, the compositions comprise a metal ion (e.g., a magnesium salt such as magnesium chloride or magnesium sulfate), one or more nucleoside triphosphates, one or more nucleic acid primers or probes, one or more additional nucleic acid polymerases or fragments thereof having desired activities, one or more polymerization detection agents (e.g., specific or non-specific dyes or fluorescent molecules), and/or one or more nucleic acid templates for amplification or sequencing. Other exemplary substances include, but are not limited to, detergents, DMSO, DMF, gelatin, glycerol, betaine, spermidine, T4 gene 32 protein, *E. coli* SSB, BSA, and ammonium sulfate.

III. NUCLEIC ACIDS, VECTORS, AND HOST CELLS

Also provided is a nucleic acid that encodes any of the mutant DNA polymerases described herein. Nucleic acids encoding the mutant DNA polymerases can be obtained using routine techniques in the field of recombinant genetics.

Vectors having one or more of the nucleotide sequences described herein are also provided. A vector refers to a nucleic acid molecule capable of transporting another nucleic acid to which it has been linked. The vector can be capable of autonomous replication or integration into a host DNA. Exemplary vectors include, but are not limited to, a plasmid, cosmid, or viral vector. The vector can include a nucleic acid in a form suitable for expression of the nucleic acid in a host cell. In some embodiments, the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as inducible regulatory sequences. The design of the expression vector can depend on such factors as the choice of the host cell to be transformed, transfected, or infected and the level of expression of protein desired. Suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

Examples of expression vectors include, but are not limited to, chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described herein can be inserted into an appropriate restriction endonuclease site(s) by procedures known in the art.

The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells (e.g., dihydrofolate reductase or neomycin resistance for eukaryotic cell cultures; tetracycline or ampicillin resistance in *E. coli*).

The vector containing the appropriate nucleic acid sequences as described herein, as well as an appropriate promoter or control sequence, can be employed to transform, transfect, or infect an appropriate host to permit the host to express the polypeptides described herein (e.g., SEQ ID NOS: 1-7). Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, methods are provided for producing the mutant DNA polymerase polypeptides described herein by transforming, transfecting, or infecting a host cell with an expression vector having a nucleotide sequence that encodes one of the polypeptides. The host cells are then cultured under a suitable condition, which allows for the expression of the polypeptide.

IV. METHODS AND USES

The mutant Type-A DNA polymerases described herein can be used in various methods to amplify a target nucleic acid. For example, the mutant Type-A DNA polymerases and compositions comprising such mutant polymerases can be used in a primer extension method or in a method of polymerizing nucleic acids from a primer or set of primers and a nucleic acid template. In an embodiment, a method of amplifying a target nucleic acid comprises contacting a test sample suspected of containing the target nucleic acid with any one of the mutant polymerases described herein, at least one primer that specifically binds to the target nucleic acid, and nucleotides to form a mixture or a composition. The mixture may be formed manually or automatically. The next step of the method comprises incubating the mixture under conditions permitting extension (or polymerization) of the at least one primer by the polymerase using the sequence of the target nucleic acid as a template for incorporation of the nucleotides.

A wide variety of nucleic acids can be subjected to copying, amplifying, or sequencing. Thus, the methods are not limited by the target nucleic acid, its sequence, or length. It is to be understood that, where amplification is desired (e.g., PCR), two primers having different sequences and having specificity for two different sequences on opposite strands of the target nucleic acid should be used. In addition, the step of exposing the combined substances to conditions that allow for polymerization can be any action that allows for polymerization. Many conditions suitable for polymerization are known in the art, and those of skill in the art may select any appropriate conditions, as the situation requires, without undue or excessive experimentation. Parameters to be considered include, but are not limited to, salt concentration, metal ion or chelator concentration, buffer concentration and identity, presence or absence of detergents and organic solvents, concentration of polymerase or other enzymes, presence or concentration of nucleotides or modified nucleotides, presence or concentration of polymerization inhibitors or terminators, presence or concentration of probes or dyes for detection of polymerization products, temperature, and length of time of exposure. In some embodiments, the conditions that allow polymerization of nucleic acids from the primer(s) are the conditions for a PCR reaction.

The polymerases are advantageously used in any variation or type of PCR reaction for amplification of nucleic acids, including both DNA and RNA amplifications. For amplification of RNA templates (e.g., mRNAs or microRNAs), an RNA-dependent DNA polymerase (e.g., a reverse transcriptase; RT) can be used to make a DNA strand complementary to the RNA template, and a DNA polymerase of the invention can be used to amplify the DNA complementary strand. Polymerase chain reactions that can be conducted using the compositions described herein include, but are not limited to, reverse transcription PCR (RT-PCR), quantitative PCR (qPCR), and digital droplet PCR (ddPCR).

In some embodiments, two or more primers having different sequences are used in the method. For example, in some embodiments two primers are used. One primer specifically binds to one strand of the template DNA and the other binds to the other strand of the template DNA, allowing for production of a double-stranded polymerization product. In some embodiments, one primer is specific for a sequence present on a single-stranded RNA template, such as an mRNA. Polymerization of a first complementary strand of the RNA from the first primer provides a template for the second primer. Subsequent to a first polymerization, the first primer can prime polymerization from either the template RNA or the DNA complement. One or more nucleic acid probes having sequence specificity for the target nucleic acid (including a complementary strand of the target, where the target is single-stranded) can be included in the method to detect the amplified target nucleic acid.

PCR methods such as qPCR and ddPCR include probes, dyes, or other substances that allow for detection of polymerization (e.g., amplification) products. Accordingly, the method can include a step of including in the polymerization reaction a substance that allows for detection of polymerization products. The method can also include one or more positive or negative control reactions to determine if the methods, or particular method steps, have been performed successfully.

V. KITS

Kits for amplifying nucleic acid according to methods described herein are also provided. The kits comprise one or more of the mutant DNA polymerases described herein. The kit may also include other components for performing amplification reactions. Other components can include, but are not limited to, a buffer (in 1× or concentrated forms), a metal ion (e.g., Me), nucleotides, primers that are specific for a control nucleic acid or for a target nucleic acid, probes that are specific for a control nucleic acid or for a target nucleic acid, a detergent, and/or a detection agent (e.g., one or more dyes or one or more fluorescent molecules) for detecting polymerization products. In some embodiments, the kit further comprises instructions for carrying out the methods described herein.

VI. EXAMPLES

Example 1: Inhibitor Tolerance

This example compares the PCR inhibitor tolerance of the mutant Taq DNA polymerases SEQ ID NOS: 1-7 to wild type Taq DNA polymerase.

PCR mixtures comprising 20 mM Tris-HCl (pH 8.4), 50 mM KCl, 0.02% (v/v) Triton-100, 10 mM MgCl2, 1 mM dNTPs (1 mM each), 0.2 µM each of primer 1 (GAAGGT-GAAGGTCGGAGTC (SEQ ID NO:17)) and primer 2 (GAAGATGGTGATGGGATTTC (SEQ ID NO:18)), 1 ng 226 bp human genomic DNA, 0.5× of SYBR Green dye, Inhibitor X and 1.7 u of polymerase in a total volume of 20 µL were subjected to the following thermocycling conditions: 2 min at 95° C. followed by 40 cycles of 10 s 95° C., 45 s 60° C. Inhibitor X concentrations tested were as follows:
  Lactoferrin (Sigma-Aldrich, L9507-10MG): 0 ng/ul, 5 ng/ul, 10 ng/ul, 15 ng/ul, 20 ng/ul, 25 ng/ul, 30 ng/ul (w/v);
  IgG (Sigma-Aldrich, 14506): 0 ng/ul, 10 ng/ul, 20 ng/ul, 30 ng/ul, 30 ng/ul, 40 ng/ul, 50 ng/ul, 60 ng/ul, (w/v);
  Plasma (Sigma-Aldrich, P9523): 0%, 1%, 2%, 3%, 5%, 6%, 8%, 10% (v/v)
  Heparin (Sigma-Aldrich, H3149): 0, 0.001, 0.002, 0.005, 0.01, 0.015, 0.02, 0.03, 0.05 UPS heparin (per 20 ul of PCR reaction).

Real time qPCR was performed on a Bio-Rad CFX96 Real-Time PCR Detection System. The results are in Table 2 below. As shown in Table 2, a "+" indicates that the delta delta Cq value of the mutant is 1-5. A "++" indicates that the delta delta Cq value of the mutant is more than 5. A "−" indicates that the delta delta Cq value is about zero (i.e., the delta Cq value is similar to that of wild-type Taq polymerase or that there is no difference in inhibitor tolerance between the mutant and wild type Taq polymerase).

TABLE 2

| Mutant | Inhibitors | | | |
|---|---|---|---|---|
| | IgG | Lactoferrin | Plasma | Heparin |
| SEQ ID NO: 1 | ++ | ++ | + | ++ |
| SEQ ID NO: 2 | ++ | ++ | ++ | − |
| SEQ ID NO: 3 | ++ | ++ | ++ | ++ |
| SEQ ID NO: 4 | ++ | ++ | ++ | ++ |
| SEQ ID NO: 5 | ++ | ++ | − | ++ |
| SEQ ID NO: 6 | ++ | ++ | + | ++ |
| SEQ ID NO: 7 | ++ | ++ | ++ | − |

The results in Table 2 show that all seven mutants exhibited tolerance to IgG and Lactoferrin. All but mutant #5 were resistant to plasma and mutant #'s 1 and 3-6 were resistant to heparin.

Example 2: Thermostability

This example compares the thermostability of the mutant Taq DNA polymerases SEQ ID NOS: 1-7 to wild type Taq DNA polymerase.

PCR mixtures comprising 20 mM Tris-HCl (pH 8.4), 50 mM KCl, 0.02% (v/v) Triton X-100, 10 mM MgCl2, 1 mM dNTPs (1 mM each), 0.2 µM each of primer 1 (GAAGGT-GAAGGTCGGAGTC (SEQ ID NO:17)) and primer 2 (GAAGATGGTGATGGGATTTC (SEQ ID NO:18)), 1 ng 226 bp human genomic DNA, 0.5× of SYBR Green dye, 1.7 u of polymerase in a total volume of 20 µL were subjected to the following thermocycling conditions: 15 min at 98° C. followed by 40 cycles of 10 seconds at 98° C. and 45 seconds at 60° C. Real time qPCR was performed on a Bio-Rad CFX96 Real-Time PCR Detection System. The results are shown in Table 3 below. In Table 3, a "+" indicates that the mutant Taq DNA polymerase had a delta Cq=0 when heated at 98° C. for 15 minutes (i.e., Cq after heat treatment−Cq before heat treatment=0), whereas the delta Cq of wild-type Taq DNA polymerase was greater than zero after such heating conditions. A "−" indicates that the delta Cq of the mutant Taq DNA polymerase was similar to that of wild type Taq polymerase after such heating conditions.

TABLE 3

| Mutant | Thermostability |
|---|---|
| SEQ ID NO: 1 | − |
| SEQ ID NO: 2 | − |
| SEQ ID NO: 3 | + |
| SEQ ID NO: 4 | + |
| SEQ ID NO: 5 | + |
| SEQ ID NO: 6 | − |
| SEQ ID NO: 7 | + |

The results show that, of the mutants tested, mutant #'s 3-5 and 7 were thermostable at 98° C. for 15 minutes.

All patents, patent applications, and other published reference materials cited in this specification are hereby incorporated herein by reference in their entirety.

SEQUENCE LISTING

SEQ ID NOS: 1-8 are shown in FIG. 1.
Nucleotide sequence listing of Mutant DNA Polymerase #1: SEQ ID #9
```
ATGCTGCCGCTGTTTGAGCCGAAAGGTCGTGTGCTGCTGGTTGACGGTCATCATC
TGGCGTATCGTAACTTCTTTACGCTGAAAGGTCCGACCACCAGCCGTGGTGAGC
CGGTGCAAGGTGTTTACGGCTTCGCGAAAAGCCTGGCGAAGGCGCTGAAAGAA
GACGGCGATGTGGTTATCGTGGTTTTCGACGCGAAAGCGCCGAGCTTTCGTCAC
GAGGCGTACGGTGCGTATAAAGCGGGTCGTGCGCCGACCCCGGAGGACTTCCC
GCGTCAGCTGGCCTGATGAAGGAACTGGTGGATCTGCTGGGTCTGGAGCGTCT
GGAAGTTCCGGGCTTTGAAGCGGATGATGTTCTGGCGGCGCTGGCGAAGATAG
CGGAGCGTGAGGGTTACGAAGTGCGTATTCTGACCGCGGACCGTGACCTGTTCC
AACTGCTGAGCGACCGTATCGCGCTTCTGCACCCGGAAGGTCACCTGATTACCC
CGGGCTGGCTGTGGGAGCGTTATGGTCTGCGTCCGGAACAGTGGGTGGATTTTC
GTGCGCTGGCGGGTGACCCGAGCGATAACATCCCGGGCGTTAAAGGTATTAGC
GAGAAGATCGCGCTGAAGCTGCTGAAAGAGTGGGGCAGCCTGGAAAACATCC
AGAAAAACCTGGCTCAGGTGAAGCCGGAACGTGTTCGTGAGGCGATTCGTAAC
AACCTGGACAAGCTGCAAATGAGCCTGGAACTGAGCCGTCTGCGTACCGACCT
GCCGCTGGAAGTTGATTTCCGTCGTCGTCGTGAACCGGATCGTGAGGGTCTGGG
TGCGTTCCTGGAACGTCTGGAGTTTGGTAGCCTGCTGCACGAATTTGGCCTCTTA
GAATCACCCAAAGCCCTGGAAGAAGCACTGTGGCCTCCACCTGAAGGCGCCTT
TGTTGGTTTTGTTTGTCTCGTAAAGAACCTATGTGGGCCGATTTACTGGCCTTAG
CCGCTGCACGTGGTGGTCGTGTCCATCGCGCACCAGAACCTTATAAAGCACTGC
GTGATCTTAAAGAAGCTCGTGGTCTCCTCGCCAAAGACTTATCCGTATTAGCAC
TCCGCGAGGGTTTAGGGCTGCCACCTGGTGATGATCCAATGTTACTTGCATATCT
CCTGGATCCCTCTAATACAACCCCGGAAGGCGTGGCTCGTCGTTATGGTGATGA
ATGGACTGAAGAAGCTGGTGAACGTGCGGCTTTGTCTGAACGCTTATTCGCTGA
CCTGTGGGGCCGTCTGGAAGGAGAGGAACGCTTACTCTGGTTATATCGTGAAGT
TGAACGCCCACTGTCAGCAGTACTTGCGCACATGGAAGCTACCGGGGTCCGCTT
AGATGTTGCCTATCTCCGTGCTCTGAGTCTTGAAGTAGCCGAAGAGATTGCGCG
CCTAGAAGCCGAAGTATTTCGTCTGGCCGGTCACCCGTTCAACCTTAATTCCCGT
GATCAACTGGAACGCGTTTTGTTTGATGAACTTGGCCTGCCCGCAATTGGTAAA
ACTGAAAAAACTGGTAAACGTTCGACCTCCGCCGCAGTCCTTGAAGCCCTGCGT
GAAGCCCACCCAATTGTCGAAAAAATCCTGCAGTACCGCGAACTCACTAAACT
TAAATCTACCTATATTGACCCGCTGCCGCGTCTGGTGCACCCGAAAACCGGACG
TCTTCACACCCGTTTTAATCAAACTGCTACCGCGACTGGACGTTTAAGCTCATCC
GATCCCAACTTGCAAAATATTCCTGTCCGTACCCCACTAGGGCAACGTATTCGC
CGCGCATTTATCGCAGAGGAAGGTTGGTTGCTGGTGGCATTAGATTATAGCCAA
ATTGAATTACGTGTTCTTGCGCATTTATCCGGTGACGAAAATCTCATTCGTGTTTT
TCAGGAGGGACGTGATATTCACACAGAAACCGCTTCATGGATGTTTGGTGTTCC
GCGTGAAGCCGTCGACCCGTTAATGCGTCGCGCTGCAAAAACCATTAATTTCGG
TGTTCTGTATGGTATGAGTGCACATCGGTTATCACAAGAACTCGCTATCCCGTAC
GAAGAAGCTCAAGCATTTATTGAACGTTATTTTCAGAGTTTTTCCTAAGGTTCGTG
CGTGGATCGCGCACACCCTGGAAGAGGGTCGTAAGAAAGGCTACGTGGAGACC
CTGTTCGGTCGTCGTCGTTACGTTCCGGACCTGAACGCGCGTGTGAAAAGCGTT
CGTGAAGCGGCGGAGCGTATGGCGTTCAACATGGCGGTGCAAGGTACCGCGGC
GGACCTGATGAAGCTGGCGATGGTGAAGCTGTTTCCGCGTCTGCCGGAAGTGGG
TGCGCGTATGCTGCTGCAGGTGCACGATGAACTGCTGCTGGAGGCGCCGAAAG
AGCGTGCGGAAGAGGCGGCGGCGCTGGCGAAGGAAGTGATGGAGGGTGTTTG
GCCGCTGGCGGTGCCGCTGGAAGTGGAAGTTGGTATCGGTGAAGACTGGCTGA
GCGCGAAGGGCTAA
```

Nucleotide sequence listing of Mutant DNA Polymerase #2: SEQ ID #10
```
ATGCTGCCGCTGTTTGAGCCGAAAGGTCGTGTGCTGCTGGTTGACGGTCATCATC
TGGCGTATCGTAACTTCTTTACGCTGAAAGGTCTGACCACCAGCCGTGGTGAGC
CGGTGCAAGGTGTTTACGGCTTCGCGAAAAGCCTGGCGAAGGCGCTGAAAGAA
GACGGCGATGTGGTTATCGTGGTTTTCGACGCGGAAGCGCCGAGCTTTCGTCAC
GAGGCGTACGGTGCGTATAAAGCGGGTCGTGCGCCGACCCGGGAGGACTTCCC
GCGTCAGCTGGCGCTGATGAAGGAACTGGTGGATCTGCTGGGTCTGGAACGTCT
GGAAGTTCCGGGCTTTGAAGCGGATGATGTTCTGGCGGCGCTGGCGAAGATAG
CGGAACGTGAGGGTTACGAAGTGCGTATTCTGACCGCGGACCGTGACCTGTTCC
AACTGCTGAGCGACCGTATCGCGGTTCTGCACCCGGAAGGTCACCTGATTACCC
CGGGCTGGCTGTGGGAGCGTTATGGTCTGCGTCCGGAACAGTGGGTGGATTTTC
GTGCGCTGGCGGGTGACCCTAGCGATAACATCCCGGGCGTTAAAGGTATTAGC
GAGAAGACCGCGCTGAAGCTGCTGAAAGAGTGGGGCAGCCTGGAAAACATCC
AGAAAAACCTGGCTCAGGTGAAGCCGGAACGTGTTCGTGAGGCGATTCGTAAC
AACCTGGACAAGCTGCAAATGAGCCTGGAACTGAGCCGTCTGCGTACCGACCT
GCCGCTGGAAGTTGATTTCCGTCGTCGTCGTAAACCGGATCGTGAGGGTCTGCG
TGCATTCATGGAACGTCTGGAGTTTGATAGCCTGCTGCACGAATTTGGCCTCTTA
GAATCACCCAAGGCCCTGGAAGAAGCACTGTGGCCCCACCTGAAGGCGCCTT
TGTTGGTTTTGTTTGTCTCGTAAAGAACCTATGTGGGCCGATTTACTGGCCTTAG
CCGCTGCACGTGGTGGTCGTGTCCATCGCGCACCAGAACCTTATAAAGCACTGC
GTGATCTTAAAGAAGCTCGTGGTCTCCTCGCCAAAGACTTATCCGTATTAGCAC
TCCGCGAGGGTTTAGGGCTGCCACCTGGTGATGATCCAATGTTACTTGCATATCT
CCTGGATCCCTCTAATACAACCCCGGAAGGCGTGGCTCGTCGTTATGGTGGTGA
ATGGACTGAAGAAGCTGGTGAACGTGCGCTTTGTCTGAACGCTTATTCGCTGA
CCTGTGGGGCCGTCTGGAAGAAGAGGAACGCTTACTCTGGTTATATCATGAAGT
TGAACGCCCACTGTCAGCAGTACTTGCGCACATGGAAGCTACCGGGGTCCGCTT
AGATGTTGCCTATCTCCGTGCTCTGAGTCTTGAAGTAGCCGAAGAAATTGCGCG
CCTGGAAGCCGAAGTATTTCGTCTGGCGGGCCACCCGTTTAACCTGAACAGCCG
TGACCAGCTGGAACGTGTTCTGTTTGATGAACTGGGTCTGCCGCCGATCGGCAA
```

```
GACCGAGAAAACCGGTAAACGTAGCACCAGCGCGGCGGTGCTGGAAGCGCTG
CGTGAGGCGCACCCGATCGTTGAGAAGATTCTGCAATACCGTGAACTGGCGAA
GCTGAAAAGCACCTATATTGACCCGCTGCCGCGTCTGGTGCACCCGAAAACCG
GTCGTCTGCACACCCGTTTCAACCAAACCGCGACCGCGACCGGCCGTCTGAGCA
GCAGCGATCCGAACCTGCAGAACATCCCGGTTCGTACCCCGCTGGGTCAACGT
ATCCGTAAGGCGTTTATCGCAGAAGAAGGTTGGCTGCTGGTGGCATTAGATTAT
AGCCAAATTGAACTGCGTGTTCTGGCGCACCTGAGCGGTGACGAGAACCTGATC
CGTGTGTTCCGTGAAGGCAAAGATATTCACACCGAGACCGCTTCATGGATGTTT
GGTGTTCCGCGTGAAGCCGTCGACCCGTTAATGCGTCGCGCTGCAAAACCATT
AATTTTGGTGTTCTGTATGGTATGAGCGCGCACCGTCTGAGCCAGGAACTGAGC
ATCCCGTATGAAGAGGCGGCGGCGTTTATTGAGCGTTATTTCCAGCGCTTTCCGC
AAGTGCGTGCGTGGATCGCGCACACCCTGGAAGAGGGTCGTAAGAAAGGCTAC
GTGGAGACCCTGTTCGGTCGTCGTCGTTACGTTCCGGACCTGAACGCGCGTGTG
AAAAGCGTTCGTGAAGCAGCGGAGCGTATGGCGTTCAACATGGCGGTGCAAGG
TACCGCGGCGGACCTGATGAAGCTGGCGATGGTGAAGCTGTTTCCGCGTCTGCG
TCCGCTGGGCGTTCGTATGCTGCTGCAGGTTCACGATGAACTGCTGCTGGAGGC
GCCGAAAGAGCGTGCGGAAGAGGCGGCGGCGCTGGCGAAGGAAGTGATGGAG
GGTGTTTGGCCGCTGGCGGTGCCGCTGGAAGTGGAAGTTGGTATCGGTGAAGAC
TGGCTGAGCGCGAAGGGCTAATATCTAACTAAGCTTGACCTGTGAAGTGAAAA
ATGGCGCACATGGCGACATT

Nucleotide sequence listing of Mutant DNA Polymerase #3: SEQ ID #11
ATGCTGCCGCTGTTTGAGCCGAAAGGTCGTGTGCTGCTGGTTGACGGTCATCATC
TGGCGTATCGTAACTTCTTTACGCTGAGAGGTCTGACCACCAGCCGTGGTGAGC
CTGTGCAAGGTGTTTACGGCTTCGCGAAAAGCCTGGCGAAGGCGCTGAAAGAA
GACGGCGATGTGGTTATCGTGGTTTTCGACGCGAAAGCGCCGAGCTTTCGTCAC
GAGGCGTACGGTGCGTATAAAGCGGGTCGTGCGCCGACCCCGGAGGACTTCCC
GCGTCAGCTGGCGCTGATGAAGGAACTGGTGGATCTGCTGGGTCTGGAGCGTCT
GGAAGTTCCGGGCCTTGAAGCGGATGATGTTTTGGCGGCGCTGGCGAAGATAG
CGGAACGTGAGGGTTACGAAGTGCGTATTCTGACCGCGGACCGTGACCTGTTCC
AACTGCTGAGCGACCGTATCGCGGTTCTGCACCCGGAAGGTCACCTGATTACCC
CGGGCTGGCTGTGGGAGCGTTATGGTCTGCGTCCGGAACAGTGGGTGGATTTTC
GTGCGCTGACGGGTGACCCGAGCGATAACATCCCGGGCGTTAAAGGTATTGGC
GAGAAGACCGCGCTGAAGCTGCTGAAAGAGTGGGGCAGCCTGGAAAACATCC
AGAAAAACCTGGATCAGGTGAAGCCGGAACGTGTTCGTGAGGCGATTCGTAAC
AACCTGGACAAGCTGCAAATGAGCCTGGAACTGAGCCGTCTGCGTACCGACCT
GCCGCTGGAAGTTGATTTCCGTCGTCGTCGTGAACCGGATCGTGAGGGTCTGCG
TGCGTTCCTGGAACGTCTGGAGTTTGGTAGCCTGCTGCACGAATTTGGCCTCTTA
GAATCACCCAAGGCCCTGGAAGAAGCACTGTGGCCTCCACCTGAAGGCGCCTT
TGTTGGTTTTGTTTTGTCTCGTAAAGAACCTATGTGGGCCGATTTACTGGCCTTAG
CCGCTGCACGTGGTGGTCGTGTCCATCGCGCACCAGAACCTTTATAAAGCACTGC
GTGACCTTAAAGAAGCTCGTGGTCTCCTCGCCAAAGACTTATCCGTATTAGCAC
TCCGCGAGGGTTTAGGGCTGCCACCTGGTGATGATCCAATGTTACTTGCATATCT
CCTGGATCCCTCTAATACAACCCCGGAAGGCGTGGCTCGTCGTTATGGTGGTGA
ATGGACTGAAGAAGCTGGTGAACGTGCGGCTTTGTCTGAACGCTTATTCGCTAA
CCTGTGGAGCCGTCTGGAAGGAGAGGAACGCTTACTCTGGTTATATCGTGAAGT
TGAACGCCCACTGTCAGTAGTACTAGCGCACATGGAAGCTACCGGGGTCCGCTT
AGATGTTGCCTATCTCCGTGCTCTGAGTCTTGAAGTAGCCGAAGAAATTGCGCG
CCTGGAAGCCGAAGTATTTCGTCTGGCGGGCCACCCGTTTAACCTGAACAGCCG
TGACCAGCTGGAACGTGTTCTGTTTGATGAACTGGGTCTGCCGCCGATCGGCAA
GACCGAGAAAACCGGTAAACGTAGCACCAGCGCGGCGGTGCTGGAAGCGCTG
CGTGAGGCGCACCCGATCGTTGAGAAGATTCTGCAATACCGTGAACTGGCGAA
GCTGAAAAGCACCTATATTGACCCGCTGCCGCGTCTGGTGCACCCGAAAACCG
GTCGTCTGCACACCCGTTTCAACCAAACCGCGACCGCGACCGGCCGTCTGAGCA
GCAGCGATCCGAACCTGCAGAACATCCCGGTTCGTACCCCGCTGGGTCAACGT
ATCCGTAAGGCGTTTATCGCAGAAGAAGGTTGGCTGCTGGTGGCATTAGATTAT
AGCCAAATTGAACTGCGTGTTCTGGCGCACCTGAGCGGTGACGAGAACCTGATC
CGTGTGTTCCGTGAAGGCAAAGATATTCACACCGAGACCGCTTCATGGATGTTT
GGTGTTCCGCGTGAAGCCGTCGACCCGTTAATGCGTCGCGCTGCAAAACCATT
AATTTTGGTGTTCTGTATGGTATGAGTGCACATCGGTTATCACAAGAACTCGCTA
TCCCGTATGAAGAAGCTCAAGCATTTATTGAACGTTATTTTCAGAGTTTTCCTAA
GGTTCGTGCTTGGATTGAAAAAACATTGGAAGAGGGTCGTCAGCGTGGCTACGT
GGAAACCCTGTTTGGTCGTCGTCGTTACGTTCCGGATCTGAACGCGCGTGTGAA
AAGGGTTCGTGAAGCGGCGAGCGTATGGCGTTCAACATGCCGGTTCAAGGTA
CCGCGGCGGACCTGATGAAGCTGGCGATGGTTCGTCTGTTCCCGCGTCTGCCGG
AAGTGGGTGCGCGTATGCTGCTGCAGGTTCACGATGAACTGCTGCTGGAGGCGC
CGAAAGAGCGTGCGGAAGAGGCGGCGGCGCTGGCGAGGGAAGTGATGGAGGG
TGTTTGGCCGCTGGCGGTGCCGCTGGAAGTGGAAGTTGGTATTGGTGAAGACTG
GCTGAGCGCGAAGGGCTAA Nucleotide sequence listing of Mutant DNA Polymerase #4: SEQ ID #12
ATGCTGCCGCTGTTTGAGCCGAAAGGTCGTGTGCTGCTGGTTGACGGTCATCATC
TGGCGTATCGTAACTTCTTTACGCTGAAAGGTCCGACCACCAGCCGTGGTGAGC
CGGTGCAAGGTGTTTACGGCTTCGCGAAAAGCCTGGCGAAGGCGCTGAAAGAA
GACGGCGATGTGGTTATCGTGGTTTTCGACGCGAAAGCGCCGAGCTTTCGTCAC
GAGACGTACGGTGCGTATAAAGCGGGTCGTGCGCCGACCCCGGAGGACTTCCC
GCGTCAGCTGGCGCTGATGAAGGAACTGGTGGATCTGCTGGGTCTGGAGCGTCT
```

SEQUENCE LISTING

```
GGAAGTTCCGGGCTTTGAAGCGGATGATGTTCTGGCGGCGCTGGCGAAGATAG
CGGAGCGTGAGGGTTACGAAGTGCGTATTCTGACCGCGGACCGTGACCTGTTCC
AACTGCTGAGCGACCGTATCGCGGTTCTGCACCCGGAAGGTCACCTGATTACCC
CGGGCTGGCTGTGGGAGCGTTATGGTCTGCGTCCGGAACAGTGGGTGGATTTTC
GTGCGCTGGCGGGTGACCCGAGCGATAACATCCCGGGCGTTAAAGGTATTGGC
GAGAAGACCGCGCTGAAGCTGCTGAAAGAGTGGGGCAGCCTGGAAAACATCC
AGAAAAAACCTGGATCAGGTGAAGCCGGAACGTGTTCGTGAGGCGATTCGTAAC
AACCTGGACAAGCTGCAAATGAGTCTGGAACTGAGCCGTCTGCGTACCGACCT
GCCGCTGGAAGTTGATTTCCGTCGTCGTCGTGAACCGGATCGTGAGGGTCTGCG
TGCGTTCCTGGAACGTCTGGAGTTTGGTAGCCTGCTGCACGAATTTGGCCTCTTA
GAATCACCCAAGGCCCTGGAAGAAGCACTGTGGCCTCCACCTGAAGGCGCCTT
TGTTGGTTTTGTTTTGTCTCGTAAAGAACCTATGTGGGCCGATTTACTGGCCTTAG
CCGCTGCACGTGGTGGTCGTGTCCATCGCGCACCAGAACCTTATAAAGCACTGC
GTGACCTTAAAGAAGCTCGTGGTCTCCTCGCCAAAGACTTATCCGTATTAGCAC
TCCGCGAGGGTTTAGGGCTGCCACCTGGTGATGATCCAATGTTACTTGCATATCT
CCTGGATCCCTCTAATACAACCCCGGAAGGCGTGGCTCGTCGTTATGGTGGTGA
ATGGACTGAAGAAGCTGGTGAACGTGCGGCTTTGTCTGAACGCTTATTCGCTAA
CCTGTGGGGCCGTCTGGAAGGAGAGGAACGCTTACTCTGGTTATATCGTGAAGT
TGAACGCCCACTGTCAGCAGTACTTGCGCACATGGAAGCTACCGGGGTCCGCTT
AGATGTTGCCTATCTCCGTGCTCTGAGTCTTGAAGTAGCCGAAGAAATTGCGCG
CCTGGAAGCCGAAGTATTTCGTCTGGCGGGCCACCCGTTTAACCTGAACAGCCG
TGACCAGCTGGAACGTGTTCTGTTTGATGAACTGGGTCTGCCGCCGATCGGCAA
GACCGAGAAACCGGTAAACGTAGCACCAGCGCGGCGGTGCTGGAAGCGCTG
CGTGAGGCGCACCCGATCGTTGAGAAGATTCTGCAATACCGTGAACTGGCGAA
GCTGAAAAGCACCTATATTGACCCGCTGCCGCGTCTGGTGCACCCGAAAACCG
GTCGTCTGCACACCCGTTTCAACCAAACCGCGACCGCGACCGGCCGTCTGAGCA
GCAGCGATCCGAACCTGCAGAACATCCCGGTTCGTACCCCGCTGGGTCAACGT
ATCCGTAAGGCGTTTATCGCAGAAGAAGGTTGGCTGCTGGTGGCATTAGATTAT
AGCCAAATTGAACTGCGTGTTCTGGCGCACCTGAGCGGTGACGAGAACCTGATC
CGTGTGTTCCGTGAAGGCAAAGATATTCACACCGAGACCGCGGCGTGGATGTTT
GGTGTGCCGCCGGAAGGTGTTGATGGTGCGATGCGTCGTGCGGCGAAGACCGT
GAACTTCGGTGTTCTGTATGGCATGAGCGCGCACCGTCTGAGCCAGGAACTGAG
CATCCCGTACGAAGAGGCGGCGGCGTTTATTGAGCGTTATTTCCAGCGCTTTCC
GCAAGTGCGTGCGTGGATCGCGCACACCCTGGAAGAGGGTCGTAAGAAAGGCT
ACGTGGAGACCCTGTTCGGTCGTCGTCGTTACGTTCCGGACCTGAACGCGCGTG
TGAAAAGCGTTCGTGAAGCAGCGGAGCGTATGGCGTTCAACATGGCGGTGCAA
GGTACCGCGGCGGACCTGATGAAGCTGGCGATGGTGAAGCTGTTTCCGCGTCTG
CCGGAAGTGGGTGCGCGTATGCTGCTGCAGGTGCACGATGAACTGCTGCTGGA
GGCGCCGAAAGAGCGTGCGGAAGAGGCGGCGGCGCTGGCGAAGGAAGTGATG
GAGGGTGTTTGGCCGCTGGCGGTGCCGCTGGAAGTGGAAGTTGGTATCGGTGAA
GACTGGCTGAGCGCGAAGGGCTAA
```

Nucleotide sequence listing of Mutant DNA Polymerase #5: SEQ ID #13
```
ATGCTGCCGCTGTTTGAGCCGAAAGGTCGTGTGCTGCTGGTTGACGGTCATCATCTG
GCGTATCGTAACTTCTTTACGCTGAAAGGTCTGACCACCAGCCGTGGTGAGCCTGG
CAAGGTGTTTACGCTTCGCGAAAAGCCTGGCGAAGGCGCTGAAAGAAGACGGCGA
TGTGGTTATCGTGGTTTTCGACGCGAAAGCGCCGAGCTTTCGTCACGAGGCGTACGG
TGCGTATAAAGCGGGTCGTGCGCCGACCCCGGAGGACTTCCCGCGTCAGCTGGCGC
TGATGAAGGAACTGGTGGATCTCCTGGGTCTGGAGCGTCTGGAAGTTCCGGGCTTTG
AAGCGGATGATGTTCTGGCGGCGCTGGCGAAGATAGCGGAACGTGAGGGTTACGAA
GTGCGTATTCTGACCGCGGACCGTGACCTGTTCCAACTGCTGAGCGACCGTATCGCG
GTTCTGCACCCGGAAGGTCACCTAATTACCCCGGGCTGGCTGTGGGAGCGTTATGGT
CTGCGTCCGGAACAGTGGGTGAATTTTCGTGCGCTGGCGGGTGACCCGAGCGATAA
CATCCCGGGCGTTAAAGGTATTGGCGAGAAGACCACGCTGAAGCTGCTGAAAGAGT
GGGGCAGCCTGGAAAACATCCAGAAAAACCTGGATCAGGTGAAGCCGGAACGTGTT
CGTGAGGCGATTCGTAACAACCTGGACAAGCTGCAAATGAGCCTGGAACTGAGCTG
TCTGCGTACCGACCTGCCGCTGGAAGTTGATTTCCGTCGTCGTCGTGAACCGGATCG
TGAGGGTCTGCGTGCGTTCCTGGAACGTCTGGAGTTTGGTAGCCTGCTGCACGAATT
TGGCCTCTTAGAGTCACCCAAGGCCCTGGAAGAAGCACTGTGGCCTCCACCTGAAG
GCGCCTTTGTTGGTTTTGTTTTGTCTCGTAAAGAACCTATGTGGGCCGATTTACTGGC
CTTAGCCGCTGCACGTGGTGGTCGTGTCCATCGCGCACCAGAACCTTATAAAGCACT
GCGTGATCTTAAAGAAGCTCGTGGTCTCCTCGCCAAAGACTTATCCGTATTAGCACT
CCGCGAGGGTTTAGGGCTGCCACCTGGTGATGATCCAATGTTACTTGCATATCTCCT
GGATCCCTCTAATACAACCCCGGAAGGCGTGGCTCGTCGTTATGGTGGTGAATGGAC
TGAAGAAGCTGGTGAACGTGCGGCTTTGTCTGAACGCTTATTCGCTAACCTGTGGGG
CCGTCTGGAAGGAGAGGAACGCTTACTCTGGTTATATCGTGAAGTTGAACGCCCACT
GTCAGCAGTACTTGCGCACATGGAAGCTACCGGGGTCCGCTTAGATGTTGCCTATCT
CCGTGCTCTGAGTCTTGAAGTAGCCGAAGAAATTGCGCGCCTGGAAGCCGAAGTATT
TCGTCTGGCGGGCCACCCGTTTAACCTGAACAGCCGTGACCAGCTGGAACGTGTTCT
GTTTGATGAACTGGGTCTGCCGCCGATCGGCAGGACCGAGAAACCGGTAAACGTA
GCACCAGCGCGGCGGTGCTGGAAGCGCTGCGTGAGGCGCACCCGATCGTTGAGAAG
ATTCTGCAATACCGTGAACTGGCGAAGCTGAAAAGCACCTATATTGACCCGCTGCCG
CGTCTGGTGCACCCGAAAACCGGTCGTCTGCACACCCGTTTCAACCAAACCGCGACC
GCGACCGGCCGTCTGAGCAGCAGCGATCCGAACCTGCAGAACATCCCGGTTCGTAC
CCCGCTGGGTCAACGTATCCGTAAGGCGTTTATCGCAGAAGAAGGTTGGCTGCTGGT
GGCATTAGATTATAGCCAAATTGAACTGCGTGTTCTGGCGCACCTGAGCGGTGACGA
GAACCTGATCCGTGTGTTCCGTGAAGGCAAAGATATTCACACCGAGACCGCTTCATG
```

| SEQUENCE LISTING |
| --- |
| GATGTTTGGTGTTCCGCGTGAAGCCGTCGACCCGTTAATGCGTCGCGCTGCAAAAAC
CATTAATTTTGGTGTTCTGTATGGTATGAGCGCGCACCGTCTGAGCCAGGAACTGAG
CATCCCGTATGAAGAGGCGGTGGCGTTTATTGAGCGTTATTTCCAGAGCTTTCCGCA
AGTGCGTGCGTGGATCGCGCACACCCTGGAAGAGGGTCGTAAGAAAGGCTACGTGG
AGACCCTGTTCGGTCGTCGTCGTTACGTTCCGGACCTGAACGCGCGTGTGAAAAGCG
TTCGTGAAGCGGCGGAGCGTATGGCGTTCAACATGGCGGTGCAAGGTACCGCGGCG
GACCTGATGAAGCTGGCGATGGTGAAGCTGTTTCCGCGTCTGCCGGAAGTGGGTGC
GCGTATGCTGCTGCAGGTGCACGATGAACTGCTGCTGGAGGCGCCGAAAGAGCGTG
CGGAAGAGGCGGCGGCGCTGGCGAAGGAAGTGATGGAGGGTGTTTGGCCGCTGGCG
GTGCCGCTGGAAGTCGAAGTGGGCATCGGTGAAGACTGGCTGTCGGCAAAaGAATA
A |

Nucleotide sequence listing of Mutant DNA Polymerase #6: SEQ ID #14
TATGCTGCCGCTGTTTGAGCCGAAAGGTCGTGTGCTGCTGGTTGACGGTCATCAT
CTGGCGCATCGTAACTTCTTCGCGCTGAAAGGTCTGACCACCAGCCGTGGTGAG
CCGGTGCAAGGTGTTTACGGCTTCGCGAAAAGCCTGCTGAAGGCGCTGAAAGA
AGACGGCGATGTGGTTATCGTGGTTTTCGACGCGAAAGCGCCGAGCTTTCGTCA
CGAGGCGTACGGTGCGTATAAAGCAGGTCGTGCGCCGACCCCGGAAGACTTCC
CGCGTCAACTGGCGCTGATTAAGGAGCTGGTTGATCTGCTGGGTCTGGTGCGTC
TGGAAGTGCCGGGCTTTGAAGCGGATGATGTGCTGGCGACCCTGGCGGAAGAA
GCAGAAAAAGAAGGATATGAAGTACGCATCCTGACAGCCGACAAAGACTTAT
ACCAAATCCTTTCAGATCGCGTCCACGTTTTACATCCCGAAGGCTACTTAATTAC
CCCTGCATGGCTGTGGGAAAAATATGGATTACGTCCGGATCAATGGGCCGATTA
CCGTGCTTTAACCGGTGATGAATCAGATAACCTGCCAGATGTTAAAGGGATTGG
AGAAAAAACTGCCTGTAAATTGTTAGATGAATGGGGCTCTTTGGAAGCACTGTT
AAAAAACCTTGATCGTCTCAAACCTGCCATCCGCGAAAAAATCCTGGCCCACA
TGGATGACTTAAAACTGAGCTGGGATCCCGCTAAAGTTCGTACCGACTTACCTC
TTGAAGTTGATTTTGCAAAACGCCGTGAACCTGATCGTGAACGCCTTCGTGCATT
TCTTGAACGTCTGGAATTTGGCTCCTTGTTACATGAATTTGGCCTCTTAGAATCA
CCCAAGGCCCTGGAAGAAGCACTGTGCCTCCACCTGAAGGCGCCTTTGTTGGT
TTTGTTTTGTCTCGTAAAGAACCTATGTGGGCCGATTTACTGGCATTAGCCGCTG
CACGTGGTGGTCGTGTCCATCGCGCACCAGAACCTTATAAAGCACTGCGTGATC
TTAAAGAAGCTCGTGGTCTCCTCGCCAAAGACTTATCCGTATTAGCACTCCGCG
AGGGTTTAGGGCTGCCACCTGGTGATGATCCAATGTTACTTGCATATCTCCTGGA
TCCCTCTAATACAACCCCGGAAGGCGTGGCTCGTCGTTATGGTGGTGAATGGAC
TGAAGAAGCTGGTGAACGTGCGGCTTTGTCTGAACGCTTATTCGCTGACCTGTG
GGGCCGTCTGGAAGGAGAGGAACGCTTACTCTGGTTATATCGTGAAGTTGAACG
CCCACTGTCAGCAGTACTTGCGCGCATGGAAGCTACCGGGGTCCGCTTAGATGT
TGCCTATCTCCGTGCTCTGAGTCTTGAAGTAGCCGAAGAAATTGCGCGCCTGGA
AGCCGAAGTATTTCGTCTGGCCGGTCACCCGTTTAACCTTAATTCCCGTGATCAA
CTGGAACGCGTTTTGTTTGATGAACTTGGCCTGCCCGCAATTGGTAAAACTGAA
AAAACTGGTAAACGTTCGACCTCCGCCGCAGTCCTTGAAGCCCTGCGTGAAGCC
CACCCAATTGTCGAAAAAATCCTGCAGTACCGGGAACTCACGAAACTTAAATC
TACCTATATTGACCCGCTGCCGCGTCTGGTGCACCCGAAAACCGGACGTCTTCA
CACCCGTTTTAATCAAACTGCTACCGCGACTGGACGTTTAAGCTCATCCGATCC
CAACTTGCAAAATATTCCTGTCCGTACCCCACTAGGGCAACGTATTCGTAAGGC
GTTTATTGCGGAAGAGGGCCACCTGCTGGTTGCGCTGGACTACAGCCAGATCGA
ACTGCGTGTTCTGGCGCACCTGAGCGGTGACGAGAACCTGATCCGTGTTTTCCA
GGAAGGCAAAGATATTCACACCGAGACCGCGGCGTGGATGTTTGGTGTGCCGC
CGGAAGGTGTTGATGGTGCGATGCGTCGTGCGGCGAAGACCGTGAACTTCGGTG
TTCTGTATGGCATGAGCGCGCACCGTCTGAGCCAGGAACTGAGCATCCCGTACG
AAGAGGCGGCGGCGTTTATTGAGCGTTATTTCCAGAGCTTTCCGCAAGTGCGTG
CGTGGATCGCGCACACCCTGGAAGAGGGTCGTAAGAAAGGCTACGTGGAGACC
CTGTTCGGTCGTCGTCGTTACGTTCCGGACCTGAACGCGCGTGTGAAAAGCGTT
CGTAAAGCGGCGGAGCGTATGGCGTTCAACATGGCGGTGCAAGGTACCGCGGC
GGACCTGATGAAGCTGGCGATGGTGAAGCTGTTTCCGCGTCTGCCGGAAGTGGG
TGCGCGTATGCTGTTGCAGGTGCACGATGAACTGCTGCTGGAGGCGCCGAAAG
AGCGTGCGGAAGAGGCGGCGGCGCTGGCGAAGGAAGTGATGGAGGGTGTTTG
GCCGCTTGCGGTGCCGCTGGAAGTGGAAGTTGGTATCGGTGAAGACTGGCTGAG
CGCGAAGGGCTAATATCTAACTAA Nucleotide sequence listing of Mutant DNA Polymerase #7: SEQ ID #15
ATGCTGCCGCTGTTTGAGCCGAAAGGTCGTGTGCTGCTGGTTGACGGCCACCAC
CTGGCGTACCGTACCTTCTTTGCGCTGAAAGGTCTGACCACCAGCCGTGGTGAG
CCGGTGCAAGGTGTTTACGGCTTCGCGAAAAGCCTGCTGAAGGCGCTGAAAGA
AGACGGCGAGGTGGCGATCGTGGTTTTCGATGCGAAAGCGCCGAGCTTTCGTCA
CGAAGCGTACGAGGCGTATAAAGCGGGTCGTGCGCCGACCCCGGAAGACTTCC
CGCGTCAACTGGCGCTGATTAAGGAGCTGGTTGATCTGCTGGGTCTGGTGCGTC
TGGAAGTGCCGGGCTTTGAAGCGGATGATGTTCTGGCGGCGCTGGCGAAGAAA
GCGGAACGTGAGGGTTACGAGGTTCGTATCCTGAGCGCGGACCGTGATCTGTAT
CAGCTGCTGAGCGACCGTATTCACCTACTGCATCCCGAAGGCTACTTAATTACC
CCTGCATGGCTGTGGGAAAAATATGGATTACGTCCGGATCAATGGGCCGATTAC
CGTGCTTTAACCGGTGATGAATCAGATAACCTGCCAGGTGTTAAAGGGATTGGA
GAAAAAACTGCCCGTAAATTGTTAGAAGAATGGGGCTCTTTGGAAGCACTGTTA
AAAAACCTTGATCGTCTCAAACCTGCCATCCGCGAAAAAATTCTGGCCCACATG
GATGACTTAAAACTGAGCTGGGATCCCGCTAAAGTTCGTACCGACTTACCTCTC
GAAGTTGATTTTGCAAAACGCCGTGAACCTGATCGTGAACGCCTTCGTGCATTT

```
CTTGAACGTCTGGAATTTGGCTCCTTGTTACACGAATTTGGCCTCTTAGAATCAC
CCAAGGCCCTGGAAGAAGCACCGTGGCCTCCACCTGAAGGCGCCTTTGTTGGTT
TTGTTTTGTCTCGTAAAGAACCTATGTGGGCCGATTTACTGGCCTTAGCCGCTGC
ACGTGGTGGTCGTGTCCATCGCGCACCAGAACCTTATAAAGCACTGCGTGATCT
TAAAGAAGCTCGTGGTCTCCTCGCCAAAGACTTATCCGTATTAGCACTCCGCGA
GGGTTTAGGGCTGCCACCTGGTGATGATCCAATGTTACTTGCATATCTCCTGGAT
CCCTCTAATACAACCCCGGAAGGCGTGGCTCGTCGTTATGGTGGTAATGGACT
GAAGAAGCTGGTGAACGTGCGGCTTTGTCTGAACGCTTATTCGCTAACCTGTGG
GGCCGTCTGGAAGGAGAGGAACGCTTACTCTGGTTATATCGTGAAGTTGAACGC
CCACTGTCAGCAGTACTTGCGCACATGGAAGCTACCGGGGTCCGCTTAGATGTT
GCCTATCTCCGTGCTCTGAGTCTTGAAGTAGCCGAAGAAATTGCGCGCCTGGAA
GCCGAAGTATTTCGTCTGGCCGGTCACCCGTTCAACCTTAATTCCCGTGATCAAC
TGGAACGCGTTTTGTTTGATGAACTTGGCCTGCCCGCAATTGGTAAAACTGAAA
AAACTGGTAAACGTTCGACCTCCGCCGCAGTCCTTGAAGCCCTGCGTGAAGCCC
ACCCAATTGTCGAAAAAATCCTGCAGTACCGCGAACTCACTAAACTTAAATCTA
CCTATATTGACCCGCTGCCGCGTCTGGTGCACCCGAAAACCGGACGTCTTCACA
CCCGTTTTAATCAAACTGCTACCGCGACTGGACGTTTAAGCTCATCCGATCCCA
ACTTGCAAAATATTCCTGTCCGTACCCCACTAGGGCAACGTATTCGCCGCGCAT
TTATCGCAGAGGAAGGTTGGTTGCTGGTGGCATTAGATTATAGCCAAATTGAAT
TACGTGTTCTTGCGCATTTATCCGGTGACGAAAATCTCATTCGTGTTTTTCAGGA
GGGACGTGATATTCACACAGAAACCGCTTCATGGATGTTTGGTGTTCCGCGTGA
AGCCGTCGACCCGTTAATGCGTCGCGCTGCAAAAACCATTAATTTCGGTGTTCT
GTATGGTATGAGTGCACATCGGTTATCACAAGAACTCGCTATCCCGTACGAAGA
AGCTCAAGCATTTATTGAACGTTATTTTCAGAGTTTTCCTAAGGTTCGTGCTTGG
ATTGAGCGTACCCTGGAAGAGGGTCGTCAGCGTGGCTACGTGGAAACCCTGTTT
GGTCGTCGTCGTTACGTTCCGGATCTGAACGCGCGTGTGAAAAGGGTTCGTAAA
GCGGCGGAGCGTATGGCGTTCAACATGCAGGTGCAAGGTACCGCGGCGGACCT
GATGAAGCTGGCGATGGTTCGTCTGTTCCCGCGTCTGCCGGAAGTGGGTGCGCG
TATGCTGCTGCAGGTTCACGATGAACTGCTGCTGGAGGCGCCGAAAGAGCGTG
CGGAAGAGGCGGCGCAACTGGCGAAGGAAACCATGGAGGGTGTTTGGCCGCTG
GCGGTGCCGCTGGAAGTCGAAGTGGGCATCGGTGAAGACTGGCTGTCGGCAAA
AGAATAA
```

The invention claimed is:

1. A mutant Type-A DNA polymerase having a sequence at least 93% identical to an amino acid sequence selected from the group consisting of SEQ ID NOs: 1, 2, 3, 4, and 5 comprising:
a mutation occurring at a position corresponding to one or more amino acid residues 551, 788, and 798 of SEQ ID NO:8,
wherein the mutant polymerase possesses a higher resistance to a polymerization activity inhibitor than SEQ ID NO:8.

2. The mutant Type-A DNA polymerase of claim 1 comprising mutations at D551R, V788L, and A798E relative to SEQ ID NO:8.

3. The mutant Type-A DNA polymerase of claim 1 comprising one or more additional mutations at one or more position corresponding to amino acid residues of SEQ ID NO:8 selected from the group consisting of 52, 99, 109, 128, 154, 259, 268, and 739, wherein the mutations at the one or more position result in an amino acid different from the amino acid that occurs at the one or more position of SEQ ID NO:8.

4. The mutant Type-A DNA polymerase of claim 3 comprising mutations at L52A, I99M, A109E, K128I, H154A, A259R, R268G, and S739R relative to SEQ ID NO:8.

5. The mutant Type-A DNA polymerase of claim 1 comprising SEQ ID NO: 1, SEQ ID NO: 2, SEQ ID NO: 3, SEQ ID NO: 4, SEQ ID NO: 5, SEQ ID NO: 6, or SEQ ID NO: 7.

6. The mutant Type-A DNA polymerase of claim 1, wherein the mutant Type-A DNA polymerase is thermostable at 98° C. for at least 15 minutes.

7. A composition comprising (i) the mutant Type-A DNA polymerase of claim 1 and (ii) one or more reagents selected from the group consisting of an aqueous buffer, a metal ion, nucleotides, a primer, a probe, a detergent, a dye, a detection agent, a target nucleic acid, an anticoagulant, and a cell lysis agent.

8. A method of amplifying a target nucleic acid, the method comprising:
contacting a test sample suspected of containing the target nucleic acid with the mutant polymerase of claim 1, at least one primer that specifically binds to the target nucleic acid, and nucleotides to form a mixture; and
incubating the mixture under conditions permitting extension of the at least one primer by the polymerase using the sequence of the target nucleic acid as a template for incorporation of the nucleotides.

9. The method of claim 8, wherein the method is PCR.

10. The method of claim 9, wherein the method is qPCR, RT-PCR, or ddPCR.

11. The method of claim 8, wherein the conditions include the presence of an inhibitor of the wild-type DNA polymerase at a concentration that is inhibitory to the wild-type DNA polymerase.

12. The method of claim 8, wherein the test sample is a blood sample or a fraction of blood.

13. A nucleic acid comprising a nucleotide sequence that encodes the mutant thermostable Type-A DNA polymerase of claim 1.

14. A vector comprising the nucleic acid of claim 13.

15. A host cell comprising the vector of claim 14.

16. A method of producing a polypeptide, the method comprising:
culturing a host cell comprising a nucleic acid comprising a nucleotide sequence that encodes the mutant Type-A DNA polymerase of claim 1 in a medium under conditions permitting expression of a polypeptide encoded by the nucleic acid; and
purifying the polypeptide from the cultured cell or medium.

17. A kit for amplifying a target nucleic acid, the kit comprising (i) the mutant thermostable Type-A DNA polymerase of claim 1 and (ii) one or more reagents selected from the group consisting of an aqueous buffer, a metal ion, a nucleotide, a primer, a probe, a detergent, a detection agent, a dye, an anticoagulant, and a cell lysis agent.

18. A mutant Type-A DNA polymerase having a sequence at least 90% identical to an amino acid sequence selected from the group consisting of SEQ ID NOs: 1, 2, 3, 4, 5, 6, and 7 comprising:
  a mutation occurring at a position corresponding to D551R relative to SEQ ID NO:8
  wherein the mutant polymerase possesses a higher resistance to a polymerization activity inhibitor than SEQ ID NO:8.

* * * * *

SEQUENCE LISTING

<160> NUMBER OF SEQ ID NOS: 18

<210> SEQ ID NO 1
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Leu Pro Leu Phe Glu Pro Lys Gly Arg Val Leu Val Asp Gly
1               5                   10                  15

His His Leu Ala Tyr Arg Asn Phe Phe Thr Leu Lys Gly Pro Thr Thr
                20                  25                  30

Ser Arg Gly Glu Pro Val Gln Gly Val Tyr Gly Phe Ala Lys Ser Leu
            35                  40                  45

Ala Lys Ala Leu Lys Glu Asp Gly Asp Val Val Ile Val Val Phe Asp
        50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
                100                 105                 110

Phe Glu Ala Asp Asp Val Leu Ala Ala Leu Ala Lys Ile Ala Glu Arg
            115                 120                 125

Glu Gly Tyr Glu Val Arg Ile Leu Thr Ala Asp Arg Asp Leu Phe Gln
        130                 135                 140

```
Leu Leu Ser Asp Arg Ile Ala Leu Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Ser Glu Lys Thr Ala Leu Lys Leu Lys Glu Trp
        195                 200                 205

Gly Ser Leu Glu Asn Ile Gln Lys Asn Leu Ala Gln Val Lys Pro Glu
        210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Lys Ala Leu Glu Glu Ala Leu Trp Pro Pro Glu Gly Ala Phe
290                 295                 300

Val Gly Phe Val Leu Ser Arg Lys Glu Pro Met Trp Ala Asp Leu Leu
305                 310                 315                 320

Ala Leu Ala Ala Ala Arg Gly Gly Arg Val His Arg Ala Pro Glu Pro
                325                 330                 335

Tyr Lys Ala Leu Arg Asp Leu Lys Glu Ala Arg Gly Leu Leu Ala Lys
            340                 345                 350

Asp Leu Ser Val Leu Ala Leu Arg Glu Gly Leu Gly Leu Pro Pro Gly
        355                 360                 365

Asp Asp Pro Met Leu Leu Ala Tyr Leu Leu Asp Pro Ser Asn Thr Thr
        370                 375                 380

Pro Glu Gly Val Ala Arg Arg Tyr Gly Gly Glu Trp Thr Glu Glu Ala
385                 390                 395                 400

Gly Glu Arg Ala Ala Leu Ser Glu Arg Leu Phe Ala Asp Leu Trp Gly
                405                 410                 415

Arg Leu Glu Gly Glu Glu Arg Leu Leu Trp Leu Tyr Arg Glu Val Glu
            420                 425                 430

Arg Pro Leu Ser Ala Val Leu Ala His Met Glu Ala Thr Gly Val Arg
        435                 440                 445

Leu Asp Val Ala Tyr Leu Arg Ala Leu Ser Leu Glu Val Ala Glu Glu
        450                 455                 460

Ile Ala Arg Leu Glu Ala Glu Val Phe Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Ala Ile Gly Lys Thr Glu Lys Thr Gly Lys Arg Ser Thr
            500                 505                 510

Ser Ala Ala Val Leu Glu Ala Leu Arg Glu Ala His Pro Ile Val Glu
        515                 520                 525

Lys Ile Leu Gln Tyr Arg Glu Leu Thr Lys Leu Lys Ser Thr Tyr Ile
        530                 535                 540

Asp Pro Leu Pro Arg Leu Val His Pro Lys Thr Gly Arg Leu His Thr
545                 550                 555                 560
```

```
Arg Phe Asn Gln Thr Ala Thr Ala Thr Gly Arg Leu Ser Ser Ser Asp
            565                 570                 575

Pro Asn Leu Gln Asn Ile Pro Val Arg Thr Pro Leu Gly Gln Arg Ile
        580                 585                 590

Arg Arg Ala Phe Ile Ala Glu Glu Gly Trp Leu Leu Val Ala Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Gln Glu Gly Arg Asp Ile His Thr Glu Thr
625                 630                 635                 640

Ala Ser Trp Met Phe Gly Val Pro Arg Glu Ala Val Asp Pro Leu Met
                645                 650                 655

Arg Arg Ala Ala Lys Thr Ile Asn Phe Gly Val Leu Tyr Gly Met Ser
                660                 665                 670

Ala His Arg Leu Ser Gln Glu Leu Ala Ile Pro Tyr Glu Glu Ala Gln
            675                 680                 685

Ala Phe Ile Glu Arg Tyr Phe Gln Ser Phe Pro Lys Val Arg Ala Trp
        690                 695                 700

Ile Ala His Thr Leu Glu Glu Gly Arg Lys Lys Gly Tyr Val Glu Thr
705                 710                 715                 720

Leu Phe Gly Arg Arg Arg Tyr Val Pro Asp Leu Asn Ala Arg Val Lys
                725                 730                 735

Ser Val Arg Glu Ala Ala Glu Arg Met Ala Phe Asn Met Ala Val Gln
                740                 745                 750

Gly Thr Ala Ala Asp Leu Met Lys Leu Ala Met Val Lys Leu Phe Pro
            755                 760                 765

Arg Leu Pro Glu Val Gly Ala Arg Met Leu Leu Gln Val His Asp Glu
        770                 775                 780

Leu Leu Leu Glu Ala Pro Lys Glu Arg Ala Glu Ala Ala Ala Leu
785                 790                 795                 800

Ala Lys Glu Val Met Glu Gly Val Trp Pro Leu Ala Val Pro Leu Glu
                805                 810                 815

Val Glu Val Gly Ile Gly Glu Asp Trp Leu Ser Ala Lys Gly
            820                 825                 830

<210> SEQ ID NO 2
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Leu Pro Leu Phe Glu Pro Lys Gly Arg Val Leu Leu Val Asp Gly
1               5                   10                  15

His His Leu Ala Tyr Arg Asn Phe Phe Thr Leu Lys Gly Leu Thr Thr
            20                  25                  30

Ser Arg Gly Glu Pro Val Gln Gly Val Tyr Gly Phe Ala Lys Ser Leu
        35                  40                  45

Ala Lys Ala Leu Lys Glu Asp Gly Asp Val Val Ile Val Val Phe Asp
    50                  55                  60

Ala Glu Ala Pro Ser Phe Arg His Glu Ala Tyr Gly Ala Tyr Lys Ala
65                  70                  75                  80

Gly Arg Ala Pro Thr Arg Glu Asp Phe Pro Arg Gln Leu Ala Leu Met
                85                  90                  95
```

```
Lys Glu Leu Val Asp Leu Leu Gly Leu Glu Arg Leu Glu Val Pro Gly
            100                 105                 110

Phe Glu Ala Asp Val Leu Ala Ala Leu Ala Lys Ile Ala Glu Arg
        115                 120                 125

Glu Gly Tyr Glu Val Arg Ile Leu Thr Ala Asp Arg Asp Leu Phe Gln
            130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Ser Glu Lys Thr Ala Leu Lys Leu Leu Lys Glu Trp
            195                 200                 205

Gly Ser Leu Glu Asn Ile Gln Lys Asn Leu Ala Gln Val Lys Pro Glu
            210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Arg Arg Arg Arg Lys Pro Asp Arg Glu Gly Leu Arg Ala Phe Met Glu
            260                 265                 270

Arg Leu Glu Phe Asp Ser Leu Leu His Glu Phe Gly Leu Leu Glu Ser
            275                 280                 285

Pro Lys Ala Leu Glu Glu Ala Leu Trp Pro Pro Glu Gly Ala Phe
            290                 295                 300

Val Gly Phe Val Leu Ser Arg Lys Glu Pro Met Trp Ala Asp Leu Leu
305                 310                 315                 320

Ala Leu Ala Ala Ala Arg Gly Gly Arg Val His Arg Ala Pro Glu Pro
                325                 330                 335

Tyr Lys Ala Leu Arg Asp Leu Lys Glu Ala Arg Gly Leu Leu Ala Lys
            340                 345                 350

Asp Leu Ser Val Leu Ala Leu Arg Glu Gly Leu Gly Leu Pro Pro Gly
            355                 360                 365

Asp Asp Pro Met Leu Leu Ala Tyr Leu Leu Asp Pro Ser Asn Thr Thr
            370                 375                 380

Pro Glu Gly Val Ala Arg Arg Tyr Gly Gly Glu Trp Thr Glu Glu Ala
385                 390                 395                 400

Gly Glu Arg Ala Ala Leu Ser Glu Arg Leu Phe Ala Asp Leu Trp Gly
                405                 410                 415

Arg Leu Glu Glu Glu Arg Leu Leu Trp Leu Tyr His Glu Val Glu
            420                 425                 430

Arg Pro Leu Ser Ala Val Leu Ala His Met Glu Ala Thr Gly Val Arg
            435                 440                 445

Leu Asp Val Ala Tyr Leu Arg Ala Leu Ser Leu Glu Val Ala Glu Glu
            450                 455                 460

Ile Ala Arg Leu Glu Ala Glu Val Phe Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510
```

Ser Ala Ala Val Leu Glu Ala Leu Arg Glu Ala His Pro Ile Val Glu
            515                 520                 525

Lys Ile Leu Gln Tyr Arg Glu Leu Ala Lys Leu Lys Ser Thr Tyr Ile
        530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Lys Ala Phe Ile Ala Glu Glu Gly Trp Leu Leu Val Ala Leu Asp
        595                 600                 605

Tyr Ser Gln Ile Glu Leu Arg Val Leu Ala His Leu Ser Gly Asp Glu
            610                 615                 620

Asn Leu Ile Arg Val Phe Arg Glu Gly Lys Asp Ile His Thr Glu Thr
625                 630                 635                 640

Ala Ser Trp Met Phe Gly Val Pro Arg Glu Ala Val Asp Pro Leu Met
                645                 650                 655

Arg Arg Ala Ala Lys Thr Ile Asn Phe Gly Val Leu Tyr Gly Met Ser
        660                 665                 670

Ala His Arg Leu Ser Gln Glu Leu Ser Ile Pro Tyr Glu Glu Ala Ala
            675                 680                 685

Ala Phe Ile Glu Arg Tyr Phe Gln Arg Phe Pro Gln Val Arg Ala Trp
        690                 695                 700

Ile Ala His Thr Leu Glu Glu Gly Arg Lys Lys Gly Tyr Val Glu Thr
705                 710                 715                 720

Leu Phe Gly Arg Arg Arg Tyr Val Pro Asp Leu Asn Ala Arg Val Lys
                725                 730                 735

Ser Val Arg Glu Ala Ala Glu Arg Met Ala Phe Asn Met Ala Val Gln
        740                 745                 750

Gly Thr Ala Ala Asp Leu Met Lys Leu Ala Met Val Lys Leu Phe Pro
            755                 760                 765

Arg Leu Arg Pro Leu Gly Val Arg Met Leu Leu Gln Val His Asp Glu
        770                 775                 780

Leu Leu Leu Glu Ala Pro Lys Glu Arg Ala Glu Glu Ala Ala Ala Leu
785                 790                 795                 800

Ala Lys Glu Val Met Glu Gly Val Trp Pro Leu Ala Val Pro Leu Glu
                805                 810                 815

Val Glu Val Gly Ile Gly Glu Asp Trp Leu Ser Ala Lys Gly
            820                 825                 830

<210> SEQ ID NO 3
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Leu Pro Leu Phe Glu Pro Lys Gly Arg Val Leu Leu Val Asp Gly
1               5                   10                  15

His His Leu Ala Tyr Arg Asn Phe Phe Thr Leu Arg Gly Leu Thr Thr
                20                  25                  30

Ser Arg Gly Glu Pro Val Gln Gly Val Tyr Gly Phe Ala Lys Ser Leu
        35                  40                  45

```
Ala Lys Ala Leu Lys Glu Asp Gly Asp Val Val Ile Val Val Phe Asp
            50                  55                  60

Ala Lys Ala Pro Ser Phe Arg His Glu Ala Tyr Gly Ala Tyr Lys Ala
 65                  70                  75                  80

Gly Arg Ala Pro Thr Pro Glu Asp Phe Pro Arg Gln Leu Ala Leu Met
                 85                  90                  95

Lys Glu Leu Val Asp Leu Leu Gly Leu Glu Arg Leu Glu Val Pro Gly
                100                 105                 110

Phe Glu Ala Asp Asp Val Leu Ala Ala Leu Ala Lys Ile Ala Glu Arg
            115                 120                 125

Glu Gly Tyr Glu Val Arg Ile Leu Thr Ala Asp Arg Asp Leu Phe Gln
        130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Thr Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Lys Pro Glu
210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Lys Ala Leu Glu Glu Ala Leu Trp Pro Pro Glu Gly Ala Phe
290                 295                 300

Val Gly Phe Val Leu Ser Arg Lys Glu Pro Met Trp Ala Asp Leu Leu
305                 310                 315                 320

Ala Leu Ala Ala Ala Arg Gly Gly Arg Val His Arg Ala Pro Glu Pro
                325                 330                 335

Tyr Lys Ala Leu Arg Asp Leu Lys Glu Ala Arg Gly Leu Leu Ala Lys
            340                 345                 350

Asp Leu Ser Val Leu Ala Leu Arg Glu Gly Leu Gly Leu Pro Pro Gly
        355                 360                 365

Asp Asp Pro Met Leu Leu Ala Tyr Leu Leu Asp Pro Ser Asn Thr Thr
370                 375                 380

Pro Glu Gly Val Ala Arg Arg Tyr Gly Gly Glu Trp Thr Glu Glu Ala
385                 390                 395                 400

Gly Glu Arg Ala Ala Leu Ser Glu Arg Leu Phe Ala Asn Leu Trp Ser
                405                 410                 415

Arg Leu Glu Gly Glu Glu Arg Leu Leu Trp Leu Tyr Arg Glu Val Glu
            420                 425                 430

Arg Pro Leu Ser Val Val Leu Ala His Met Glu Ala Thr Gly Val Arg
        435                 440                 445

Leu Asp Val Ala Tyr Leu Arg Ala Leu Ser Leu Glu Val Ala Glu Glu
    450                 455                 460
```

Ile Ala Arg Leu Glu Ala Glu Val Phe Arg Leu Ala Gly His Pro Phe
465                 470                 475                 480

Asn Leu Asn Ser Arg Asp Gln Leu Glu Arg Val Leu Phe Asp Glu Leu
            485                 490                 495

Gly Leu Pro Pro Ile Gly Lys Thr Glu Lys Thr Gly Lys Arg Ser Thr
        500                 505                 510

Ser Ala Ala Val Leu Glu Ala Leu Arg Glu Ala His Pro Ile Val Glu
        515                 520                 525

Lys Ile Leu Gln Tyr Arg Glu Leu Ala Lys Leu Lys Ser Thr Tyr Ile
530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
            565                 570                 575

Pro Asn Leu Gln Asn Ile Pro Val Arg Thr Pro Leu Gly Gln Arg Ile
            580                 585                 590

Arg Lys Ala Phe Ile Ala Glu Glu Gly Trp Leu Leu Val Ala Leu Asp
            595                 600                 605

Tyr Ser Gln Ile Glu Leu Arg Val Leu Ala His Leu Ser Gly Asp Glu
            610                 615                 620

Asn Leu Ile Arg Val Phe Arg Glu Gly Lys Asp Ile His Thr Glu Thr
625                 630                 635                 640

Ala Ser Trp Met Phe Gly Val Pro Arg Glu Ala Val Asp Pro Leu Met
                645                 650                 655

Arg Arg Ala Ala Lys Thr Ile Asn Phe Gly Val Leu Tyr Gly Met Ser
            660                 665                 670

Ala His Arg Leu Ser Gln Glu Leu Ala Ile Pro Tyr Glu Glu Ala Gln
            675                 680                 685

Ala Phe Ile Glu Arg Tyr Phe Gln Ser Phe Pro Lys Val Arg Ala Trp
            690                 695                 700

Ile Glu Lys Thr Leu Glu Glu Gly Arg Gln Arg Gly Tyr Val Glu Thr
705                 710                 715                 720

Leu Phe Gly Arg Arg Arg Tyr Val Pro Asp Leu Asn Ala Arg Val Lys
                725                 730                 735

Arg Val Arg Glu Ala Ala Glu Arg Met Ala Phe Asn Met Pro Val Gln
            740                 745                 750

Gly Thr Ala Ala Asp Leu Met Lys Leu Ala Met Val Arg Leu Phe Pro
            755                 760                 765

Arg Leu Pro Glu Val Gly Ala Arg Met Leu Leu Gln Val His Asp Glu
            770                 775                 780

Leu Leu Leu Glu Ala Pro Lys Glu Arg Ala Glu Glu Ala Ala Ala Leu
785                 790                 795                 800

Ala Arg Glu Val Met Glu Gly Val Trp Pro Leu Ala Val Pro Leu Glu
                805                 810                 815

Val Glu Val Gly Ile Gly Glu Asp Trp Leu Ser Ala Lys Gly
            820                 825                 830

<210> SEQ ID NO 4
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Leu Pro Leu Phe Glu Pro Lys Gly Arg Val Leu Val Asp Gly
1               5                   10                  15

His His Leu Ala Tyr Arg Asn Phe Phe Thr Leu Lys Gly Pro Thr Thr
                20                  25                  30

Ser Arg Gly Glu Pro Val Gln Gly Val Tyr Gly Phe Ala Lys Ser Leu
            35                  40                  45

Ala Lys Ala Leu Lys Glu Asp Gly Asp Val Val Ile Val Val Phe Asp
    50                  55                  60

Ala Lys Ala Pro Ser Phe Arg His Glu Thr Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Ile Ala Glu Arg
            115                 120                 125

Glu Gly Tyr Glu Val Arg Ile Leu Thr Ala Asp Arg Asp Leu Phe Gln
130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
            195                 200                 205

Gly Ser Leu Glu Asn Ile Gln Lys Asn Leu Asp Gln Val Lys Pro Glu
210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
            275                 280                 285

Pro Lys Ala Leu Glu Glu Ala Leu Trp Pro Pro Glu Gly Ala Phe
290                 295                 300

Val Gly Phe Val Leu Ser Arg Lys Glu Pro Met Trp Ala Asp Leu Leu
305                 310                 315                 320

Ala Leu Ala Ala Ala Arg Gly Gly Arg Val His Arg Ala Pro Glu Pro
                325                 330                 335

Tyr Lys Ala Leu Arg Asp Leu Lys Glu Ala Arg Gly Leu Leu Ala Lys
            340                 345                 350

Asp Leu Ser Val Leu Ala Leu Arg Glu Gly Leu Gly Leu Pro Pro Gly
            355                 360                 365

Asp Asp Pro Met Leu Leu Ala Tyr Leu Leu Asp Pro Ser Asn Thr Thr
370                 375                 380

Pro Glu Gly Val Ala Arg Arg Tyr Gly Gly Glu Trp Thr Glu Glu Ala
385                 390                 395                 400

Gly Glu Arg Ala Ala Leu Ser Glu Arg Leu Phe Ala Asn Leu Trp Gly
                405                 410                 415
```

```
Arg Leu Glu Gly Glu Glu Arg Leu Leu Trp Leu Tyr Arg Glu Val Glu
            420                 425                 430

Arg Pro Leu Ser Ala Val Leu Ala His Met Glu Ala Thr Gly Val Arg
        435                 440                 445

Leu Asp Val Ala Tyr Leu Arg Ala Leu Ser Leu Glu Val Ala Glu Glu
    450                 455                 460

Ile Ala Arg Leu Glu Ala Glu Val Phe Arg Leu Ala Gly His Pro Phe
465                 470                 475                 480

Asn Leu Asn Ser Arg Asp Gln Leu Glu Arg Val Leu Phe Asp Glu Leu
            485                 490                 495

Gly Leu Pro Pro Ile Gly Lys Thr Glu Lys Thr Gly Lys Arg Ser Thr
        500                 505                 510

Ser Ala Ala Val Leu Glu Ala Leu Arg Glu Ala His Pro Ile Val Glu
    515                 520                 525

Lys Ile Leu Gln Tyr Arg Glu Leu Ala Lys Leu Lys Ser Thr Tyr Ile
530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
            565                 570                 575

Pro Asn Leu Gln Asn Ile Pro Val Arg Thr Pro Leu Gly Gln Arg Ile
        580                 585                 590

Arg Lys Ala Phe Ile Ala Glu Gly Trp Leu Leu Val Ala Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Arg Glu Gly Lys Asp Ile His Thr Glu Thr
625                 630                 635                 640

Ala Ala Trp Met Phe Gly Val Pro Pro Glu Gly Val Asp Gly Ala Met
            645                 650                 655

Arg Arg Ala Ala Lys Thr Val Asn Phe Gly Val Leu Tyr Gly Met Ser
        660                 665                 670

Ala His Arg Leu Ser Gln Glu Leu Ser Ile Pro Tyr Glu Glu Ala Ala
    675                 680                 685

Ala Phe Ile Glu Arg Tyr Phe Gln Arg Phe Pro Gln Val Arg Ala Trp
690                 695                 700

Ile Ala His Thr Leu Glu Glu Gly Arg Lys Lys Gly Tyr Val Glu Thr
705                 710                 715                 720

Leu Phe Gly Arg Arg Tyr Val Pro Asp Leu Asn Ala Arg Val Lys
            725                 730                 735

Ser Val Arg Glu Ala Ala Glu Arg Met Ala Phe Asn Met Ala Val Gln
        740                 745                 750

Gly Thr Ala Ala Asp Leu Met Lys Leu Ala Met Val Lys Leu Phe Pro
    755                 760                 765

Arg Leu Pro Glu Val Gly Ala Arg Met Leu Leu Gln Val His Asp Glu
770                 775                 780

Leu Leu Leu Glu Ala Pro Lys Glu Arg Ala Glu Glu Ala Ala Leu
785                 790                 795                 800

Ala Lys Glu Val Met Glu Gly Val Trp Pro Leu Ala Val Pro Leu Glu
            805                 810                 815

Val Glu Val Gly Ile Gly Glu Asp Trp Leu Ser Ala Lys Gly
        820                 825                 830
```

```
<210> SEQ ID NO 5
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

Met Leu Pro Leu Phe Glu Pro Lys Gly Arg Val Leu Val Asp Gly
1               5                   10                  15

His His Leu Ala Tyr Arg Asn Phe Phe Thr Leu Lys Gly Leu Thr Thr
            20                  25                  30

Ser Arg Gly Glu Pro Val Gln Gly Val Tyr Gly Phe Ala Lys Ser Leu
        35                  40                  45

Ala Lys Ala Leu Lys Glu Asp Gly Asp Val Val Ile Val Val Phe Asp
    50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Ile Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asn Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Lys Pro Glu
    210                 215                 220

Arg Val Arg Glu Ala Ile Arg Asn Asn Leu Asp Lys Leu Gln Met Ser
225                 230                 235                 240

Leu Glu Leu Ser Cys Leu Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Lys Ala Leu Glu Glu Ala Leu Trp Pro Pro Glu Gly Ala Phe
    290                 295                 300

Val Gly Phe Val Leu Ser Arg Lys Glu Pro Met Trp Ala Asp Leu Leu
305                 310                 315                 320

Ala Leu Ala Ala Ala Arg Gly Gly Arg Val His Arg Ala Pro Glu Pro
                325                 330                 335

Tyr Lys Ala Leu Arg Asp Leu Lys Glu Ala Arg Gly Leu Leu Ala Lys
            340                 345                 350

Asp Leu Ser Val Leu Ala Leu Arg Glu Gly Leu Gly Leu Pro Pro Gly
        355                 360                 365

```
Asp Asp Pro Met Leu Leu Ala Tyr Leu Leu Asp Pro Ser Asn Thr Thr
    370                 375                 380

Pro Glu Gly Val Ala Arg Arg Tyr Gly Gly Glu Trp Thr Glu Ala
385                 390                 395                 400

Gly Glu Arg Ala Ala Leu Ser Glu Arg Leu Phe Ala Asn Leu Trp Gly
                    405                 410                 415

Arg Leu Glu Gly Glu Arg Leu Leu Trp Leu Tyr Arg Glu Val Glu
                420                 425                 430

Arg Pro Leu Ser Ala Val Leu Ala His Met Glu Ala Thr Gly Val Arg
                    435                 440                 445

Leu Asp Val Ala Tyr Leu Arg Ala Leu Ser Leu Glu Val Ala Glu Glu
450                 455                 460

Ile Ala Arg Leu Glu Ala Glu Val Phe Arg Leu Ala Gly His Pro Phe
465                 470                 475                 480

Asn Leu Asn Ser Arg Asp Gln Leu Glu Arg Val Leu Phe Asp Glu Leu
                    485                 490                 495

Gly Leu Pro Pro Ile Gly Arg Thr Glu Lys Thr Gly Lys Arg Ser Thr
                500                 505                 510

Ser Ala Ala Val Leu Glu Ala Leu Arg Glu Ala His Pro Ile Val Glu
            515                 520                 525

Lys Ile Leu Gln Tyr Arg Glu Leu Ala Lys Leu Lys Ser Thr Tyr Ile
530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
                580                 585                 590

Arg Lys Ala Phe Ile Ala Glu Glu Gly Trp Leu Leu Val Ala Leu Asp
                595                 600                 605

Tyr Ser Gln Ile Glu Leu Arg Val Leu Ala His Leu Ser Gly Asp Glu
610                 615                 620

Asn Leu Ile Arg Val Phe Arg Glu Gly Lys Asp Ile His Thr Glu Thr
625                 630                 635                 640

Ala Ser Trp Met Phe Gly Val Pro Arg Glu Ala Val Asp Pro Leu Met
                645                 650                 655

Arg Arg Ala Ala Lys Thr Ile Asn Phe Gly Val Leu Tyr Gly Met Ser
                660                 665                 670

Ala His Arg Leu Ser Gln Glu Leu Ser Ile Pro Tyr Glu Glu Ala Val
            675                 680                 685

Ala Phe Ile Glu Arg Tyr Phe Gln Ser Phe Pro Gln Val Arg Ala Trp
            690                 695                 700

Ile Ala His Thr Leu Glu Glu Gly Arg Lys Lys Gly Tyr Val Glu Thr
705                 710                 715                 720

Leu Phe Gly Arg Arg Arg Tyr Val Pro Asp Leu Asn Ala Arg Val Lys
                725                 730                 735

Ser Val Arg Glu Ala Ala Glu Arg Met Ala Phe Asn Met Ala Val Gln
                740                 745                 750

Gly Thr Ala Ala Asp Leu Met Lys Leu Ala Met Val Lys Leu Phe Pro
            755                 760                 765

Arg Leu Pro Glu Val Gly Ala Arg Met Leu Leu Gln Val His Asp Glu
770                 775                 780

Leu Leu Leu Glu Ala Pro Lys Glu Arg Ala Glu Glu Ala Ala Ala Leu
```

```
            785                 790                 795                 800
Ala Lys Glu Val Met Glu Gly Val Trp Pro Leu Ala Val Pro Leu Glu
                    805                 810                 815

Val Glu Val Gly Ile Gly Glu Asp Trp Leu Ser Ala Lys Glu
                820                 825                 830

<210> SEQ ID NO 6
<211> LENGTH: 829
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Leu Pro Leu Phe Glu Pro Lys Gly Arg Val Leu Leu Val Asp Gly
1               5                   10                  15

His His Leu Ala His Arg Asn Phe Phe Ala Leu Lys Gly Leu Thr Thr
                20                  25                  30

Ser Arg Gly Glu Pro Val Gln Gly Val Tyr Gly Phe Ala Lys Ser Leu
            35                  40                  45

Leu Lys Ala Leu Lys Glu Asp Gly Asp Val Val Ile Val Val Phe Asp
50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Val Arg Leu Glu Val Pro Gly
                100                 105                 110

Phe Glu Ala Asp Asp Val Leu Ala Thr Leu Ala Lys Lys Ala Glu Lys
            115                 120                 125

Glu Gly Tyr Glu Val Arg Ile Leu Thr Ala Asp Lys Asp Leu Tyr Gln
130                 135                 140

Ile Leu Ser Asp Arg Val His Val Leu His Pro Glu Gly Tyr Leu Ile
145                 150                 155                 160

Thr Pro Ala Trp Leu Trp Glu Lys Tyr Gly Leu Arg Pro Asp Gln Trp
                165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Arg Lys Leu Leu Glu Glu Trp
        195                 200                 205

Gly Ser Leu Glu Ala Leu Leu Lys Asn Leu Asp Arg Leu Lys Pro Ala
    210                 215                 220

Ile Arg Glu Lys Ile Leu Ala His Met Asp Asp Leu Lys Leu Ser Trp
225                 230                 235                 240

Asp Pro Ala Lys Val Arg Thr Asp Leu Pro Leu Glu Val Asp Phe Ala
                245                 250                 255

Lys Arg Arg Glu Pro Asp Arg Glu Arg Leu Arg Ala Phe Leu Glu Arg
            260                 265                 270

Leu Glu Phe Gly Ser Leu Leu His Glu Phe Gly Leu Leu Glu Ser Pro
        275                 280                 285

Lys Ala Leu Glu Glu Ala Leu Trp Pro Pro Glu Gly Ala Phe Val
    290                 295                 300

Gly Phe Val Leu Ser Arg Lys Glu Pro Met Trp Ala Asp Leu Leu Ala
305                 310                 315                 320
```

Leu Ala Ala Ala Arg Gly Gly Arg Val His Arg Ala Pro Glu Pro Tyr
            325                 330                 335

Lys Ala Leu Arg Asp Leu Lys Glu Ala Arg Gly Leu Leu Ala Lys Asp
        340                 345                 350

Leu Ser Val Leu Ala Leu Arg Glu Gly Leu Gly Leu Pro Pro Gly Asp
    355                 360                 365

Asp Pro Met Leu Leu Ala Tyr Leu Leu Asp Pro Ser Asn Thr Thr Pro
370                 375                 380

Glu Gly Val Ala Arg Arg Tyr Gly Gly Glu Trp Thr Glu Glu Ala Gly
385                 390                 395                 400

Glu Arg Ala Ala Leu Ser Glu Arg Leu Phe Ala Asp Leu Trp Gly Arg
                405                 410                 415

Leu Glu Gly Glu Glu Arg Leu Leu Trp Leu Tyr Arg Glu Val Glu Arg
            420                 425                 430

Pro Leu Ser Ala Val Leu Ala Arg Met Glu Ala Thr Gly Val Arg Leu
        435                 440                 445

Asp Val Ala Tyr Leu Arg Ala Leu Ser Leu Glu Val Ala Glu Glu Ile
    450                 455                 460

Ala Arg Leu Glu Ala Glu Val Phe Arg Leu Ala Gly His Pro Phe Asn
465                 470                 475                 480

Leu Asn Ser Arg Asp Gln Leu Glu Arg Val Leu Phe Asp Glu Leu Gly
                485                 490                 495

Leu Pro Ala Ile Gly Lys Thr Glu Lys Thr Gly Lys Arg Ser Thr Ser
            500                 505                 510

Ala Ala Val Leu Glu Ala Leu Arg Glu Ala His Pro Ile Val Glu Lys
        515                 520                 525

Ile Leu Gln Tyr Arg Glu Leu Thr Lys Leu Lys Ser Thr Tyr Ile Asp
    530                 535                 540

Pro Leu Pro Arg Leu Val His Pro Lys Thr Gly Arg Leu His Thr Arg
545                 550                 555                 560

Phe Asn Gln Thr Ala Thr Ala Thr Gly Arg Leu Ser Ser Ser Asp Pro
                565                 570                 575

Asn Leu Gln Asn Ile Pro Val Arg Thr Pro Leu Gly Gln Arg Ile Arg
            580                 585                 590

Lys Ala Phe Ile Ala Glu Glu Gly His Leu Leu Val Ala Leu Asp Tyr
        595                 600                 605

Ser Gln Ile Glu Leu Arg Val Leu Ala His Leu Ser Gly Asp Glu Asn
    610                 615                 620

Leu Ile Arg Val Phe Gln Glu Gly Lys Asp Ile His Thr Glu Thr Ala
625                 630                 635                 640

Ala Trp Met Phe Gly Val Pro Pro Glu Gly Val Asp Gly Ala Met Arg
                645                 650                 655

Arg Ala Ala Lys Thr Val Asn Phe Gly Val Leu Tyr Gly Met Ser Ala
            660                 665                 670

His Arg Leu Ser Gln Glu Leu Ser Ile Pro Tyr Glu Glu Ala Ala Ala
        675                 680                 685

Phe Ile Glu Arg Tyr Phe Gln Ser Phe Pro Gln Val Arg Ala Trp Ile
    690                 695                 700

Ala His Thr Leu Glu Glu Gly Arg Lys Lys Gly Tyr Val Glu Thr Leu
705                 710                 715                 720

Phe Gly Arg Arg Arg Tyr Val Pro Asp Leu Asn Ala Arg Val Lys Ser
                725                 730                 735

Val Arg Lys Ala Ala Glu Arg Met Ala Phe Asn Met Ala Val Gln Gly

```
                       740                 745                 750
Thr Ala Ala Asp Leu Met Lys Leu Ala Met Val Lys Leu Phe Pro Arg
            755                 760                 765

Leu Pro Glu Val Gly Ala Arg Met Leu Leu Gln Val His Asp Glu Leu
        770                 775                 780

Leu Leu Glu Ala Pro Lys Glu Arg Ala Glu Ala Ala Ala Leu Ala
785                 790                 795                 800

Lys Glu Val Met Glu Gly Val Trp Pro Leu Ala Val Pro Leu Glu Val
                805                 810                 815

Glu Val Gly Ile Gly Glu Asp Trp Leu Ser Ala Lys Gly
                820                 825

<210> SEQ ID NO 7
<211> LENGTH: 829
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Gly Val Tyr Gly Phe Ala Lys Ser Leu
        35                  40                  45

Leu Lys Ala Leu Lys Glu Asp Gly Glu Val Ala Ile Val Val Phe Asp
50                  55                  60

Ala Lys Ala Pro Ser Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
            100                 105                 110

Phe Glu Ala Asp Asp Val Leu Ala Ala Leu Ala Lys Lys Ala Glu Arg
        115                 120                 125

Glu Gly Tyr Glu Val Arg Ile Leu Ser Ala Asp Arg Asp Leu Tyr Gln
    130                 135                 140

Leu Leu Ser Asp Arg Ile His Leu Leu His Pro Glu Gly Tyr Leu Ile
145                 150                 155                 160

Thr Pro Ala Trp Leu Trp Glu Lys Tyr Gly Leu Arg Pro Asp Gln Trp
                165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Arg Lys Leu Leu Glu Glu Trp
        195                 200                 205

Gly Ser Leu Glu Ala Leu Leu Lys Asn Leu Asp Arg Leu Lys Pro Ala
    210                 215                 220

Ile Arg Glu Lys Ile Leu Ala His Met Asp Asp Leu Lys Leu Ser Trp
225                 230                 235                 240

Asp Pro Ala Lys Val Arg Thr Asp Leu Pro Leu Glu Val Asp Phe Ala
                245                 250                 255

Lys Arg Arg Glu Pro Asp Arg Glu Arg Leu Arg Ala Phe Leu Glu Arg
            260                 265                 270
```

```
Leu Glu Phe Gly Ser Leu Leu His Glu Phe Gly Leu Glu Ser Pro
            275                 280                 285

Lys Ala Leu Glu Glu Ala Pro Trp Pro Pro Glu Gly Ala Phe Val
            290                 295                 300

Gly Phe Val Leu Ser Arg Lys Glu Pro Met Trp Ala Asp Leu Leu Ala
305                 310                 315                 320

Leu Ala Ala Ala Arg Gly Gly Arg Val His Arg Ala Pro Glu Pro Tyr
                    325                 330                 335

Lys Ala Leu Arg Asp Leu Lys Glu Ala Arg Gly Leu Leu Ala Lys Asp
            340                 345                 350

Leu Ser Val Leu Ala Leu Arg Glu Gly Leu Gly Leu Pro Pro Gly Asp
            355                 360                 365

Asp Pro Met Leu Leu Ala Tyr Leu Leu Asp Pro Ser Asn Thr Thr Pro
370                 375                 380

Glu Gly Val Ala Arg Arg Tyr Gly Gly Glu Trp Thr Glu Glu Ala Gly
385                 390                 395                 400

Glu Arg Ala Ala Leu Ser Glu Arg Leu Phe Ala Asn Leu Trp Gly Arg
                    405                 410                 415

Leu Glu Gly Glu Glu Arg Leu Leu Trp Leu Tyr Arg Glu Val Glu Arg
                    420                 425                 430

Pro Leu Ser Ala Val Leu Ala His Met Glu Ala Thr Gly Val Arg Leu
            435                 440                 445

Asp Val Ala Tyr Leu Arg Ala Leu Ser Leu Glu Val Ala Glu Glu Ile
            450                 455                 460

Ala Arg Leu Glu Ala Glu Val Phe Arg Leu Ala Gly His Pro Phe Asn
465                 470                 475                 480

Leu Asn Ser Arg Asp Gln Leu Glu Arg Val Leu Phe Asp Glu Leu Gly
                    485                 490                 495

Leu Pro Ala Ile Gly Lys Thr Glu Lys Thr Gly Lys Arg Ser Thr Ser
            500                 505                 510

Ala Ala Val Leu Glu Ala Leu Arg Glu Ala His Pro Ile Val Glu Lys
            515                 520                 525

Ile Leu Gln Tyr Arg Glu Leu Thr Lys Leu Lys Ser Thr Tyr Ile Asp
            530                 535                 540

Pro Leu Pro Arg Leu Val His Pro Lys Thr Gly Arg Leu His Thr Arg
545                 550                 555                 560

Phe Asn Gln Thr Ala Thr Ala Thr Gly Arg Leu Ser Ser Ser Asp Pro
                    565                 570                 575

Asn Leu Gln Asn Ile Pro Val Arg Thr Pro Leu Gly Gln Arg Ile Arg
            580                 585                 590

Arg Ala Phe Ile Ala Glu Glu Gly Trp Leu Leu Val Ala Leu Asp Tyr
            595                 600                 605

Ser Gln Ile Glu Leu Arg Val Leu Ala His Leu Ser Gly Asp Glu Asn
610                 615                 620

Leu Ile Arg Val Phe Gln Glu Gly Arg Asp Ile His Thr Glu Thr Ala
625                 630                 635                 640

Ser Trp Met Phe Gly Val Pro Arg Glu Ala Val Asp Pro Leu Met Arg
                    645                 650                 655

Arg Ala Ala Lys Thr Ile Asn Phe Gly Val Leu Tyr Gly Met Ser Ala
            660                 665                 670

His Arg Leu Ser Gln Glu Leu Ala Ile Pro Tyr Glu Glu Ala Gln Ala
            675                 680                 685

Phe Ile Glu Arg Tyr Phe Gln Ser Phe Pro Lys Val Arg Ala Trp Ile
```

-continued

```
              690                 695                 700
Glu Arg Thr Leu Glu Glu Gly Arg Gln Arg Gly Tyr Val Glu Thr Leu
705                 710                 715                 720

Phe Gly Arg Arg Arg Tyr Val Pro Asp Leu Asn Ala Arg Val Lys Arg
                725                 730                 735

Val Arg Lys Ala Ala Glu Arg Met Ala Phe Asn Met Pro Val Gln Gly
                740                 745                 750

Thr Ala Ala Asp Leu Met Lys Leu Ala Met Val Arg Leu Phe Pro Arg
                755                 760                 765

Leu Pro Glu Val Gly Ala Arg Met Leu Leu Gln Val His Asp Glu Leu
            770                 775                 780

Leu Leu Glu Ala Pro Lys Glu Arg Ala Glu Glu Ala Ala Gln Leu Ala
785                 790                 795                 800

Lys Glu Thr Met Glu Gly Val Trp Pro Leu Ala Val Pro Leu Glu Val
                805                 810                 815

Glu Val Gly Ile Gly Glu Asp Trp Leu Ser Ala Lys Glu
            820                 825

<210> SEQ ID NO 8
<211> LENGTH: 832
<212> TYPE: PRT
<213> ORGANISM: Thermus aquaticus

<400> SEQUENCE: 8

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Asp Ala Val Ile Val
            50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240
```

-continued

```
Leu Ser Trp Asp Leu Ala Lys Val Arg Thr Asp Leu Pro Leu Glu Val
            245                 250                 255
Asp Phe Ala Lys Arg Arg Glu Pro Asp Arg Glu Arg Leu Arg Ala Phe
        260                 265                 270
Leu Glu Arg Leu Glu Phe Gly Ser Leu Leu His Glu Phe Gly Leu Leu
    275                 280                 285
Glu Ser Pro Lys Ala Leu Glu Ala Pro Trp Pro Pro Glu Gly
290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
            325                 330                 335
Glu Pro Tyr Lys Ala Leu Arg Asp Leu Lys Glu Ala Arg Gly Leu Leu
        340                 345                 350
Ala Lys Asp Leu Ser Val Leu Ala Leu Arg Glu Gly Leu Gly Leu Pro
    355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
            405                 410                 415
Trp Gly Arg Leu Glu Gly Glu Glu Arg Leu Leu Trp Leu Tyr Arg Glu
        420                 425                 430
Val Glu Arg Pro Leu Ser Ala Val Leu Ala His Met Glu Ala Thr Gly
    435                 440                 445
Val Arg Leu Asp Val Ala Tyr Leu Arg Ala Leu Ser Leu Glu Val Ala
450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
            485                 490                 495
Glu Leu Gly Leu Pro Ala Ile Gly Lys Thr Glu Lys Thr Gly Lys Arg
        500                 505                 510
Ser Thr Ser Ala Ala Val Leu Glu Ala Leu Arg Glu Ala His Pro Ile
    515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
            565                 570                 575
Ser Asp Pro Asn Leu Gln Asn Ile Pro Val Arg Thr Pro Leu Gly Gln
        580                 585                 590
Arg Ile Arg Arg Ala Phe Ile Ala Glu Glu Gly Trp Leu Leu Val Ala
    595                 600                 605
Leu Asp Tyr Ser Gln Ile Glu Leu Arg Val Leu Ala His Leu Ser Gly
610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
            645                 650                 655
Leu Met Arg Arg Ala Ala Lys Thr Ile Asn Phe Gly Val Leu Tyr Gly
```

```
                660               665               670
Met Ser Ala His Arg Leu Ser Gln Glu Leu Ala Ile Pro Tyr Glu Glu
                    675               680               685

Ala Gln Ala Phe Ile Glu Arg Tyr Phe Gln Ser Phe Pro Lys Val Arg
        690               695               700

Ala Trp Ile Glu Lys Thr Leu Glu Glu Gly Arg Arg Gly Tyr Val
705             710               715               720

Glu Thr Leu Phe Gly Arg Arg Tyr Val Pro Asp Leu Glu Ala Arg
                    725               730               735

Val Lys Ser Val Arg Glu Ala Ala Glu Arg Met Ala Phe Asn Met Pro
                740               745               750

Val Gln Gly Thr Ala Ala Asp Leu Met Lys Leu Ala Met Val Lys Leu
            755               760               765

Phe Pro Arg Leu Glu Glu Met Gly Ala Arg Met Leu Leu Gln Val His
        770               775               780

Asp Glu Leu Val Leu Glu Ala Pro Lys Glu Arg Ala Glu Ala Val Ala
785             790               795               800

Arg Leu Ala Lys Glu Val Met Glu Gly Val Tyr Pro Leu Ala Val Pro
                    805               810               815

Leu Glu Val Glu Val Gly Ile Gly Glu Asp Trp Leu Ser Ala Lys Glu
                820               825               830

<210> SEQ ID NO 9
<211> LENGTH: 2493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgctgccgc tgtttgagcc gaaaggtcgt gtgctgctgg ttgacggtca tcatctggcg      60
tatcgtaact tctttacgct gaaaggtccg accaccagcc gtggtgagcc ggtgcaaggt     120
gtttacggct cgcgaaaaag cctggcgaag gcgctgaaag aagacggcga tgtggttatc     180
gtggttttcg acgcgaaagc gccgagcttt cgtcacgagg cgtacggtgc gtataaagcg     240
ggtcgtgcgc cgaccccgga ggacttcccg cgtcagctgg cgctgatgaa ggaactggtg     300
gatctgctgg gtctggagcg tctggaagtt ccgggctttg aagcgatgaa tgttctggcg     360
gcgctggcga agatagcgga gcgtgagggt tacgaagtgc gtattctgac cgcggaccgt     420
gacctgttcc aactgctgag cgaccgtatc gcgcttctgc acccggaagg tcacctgatt     480
aaccccgggct ggctgtggga gcgttatggt ctgcgtccgg aacagtgggt ggattttcgt     540
gcgctggcgg gtgacccgag cgataacatc ccgggcgtta aggtattag cgagaagatc     600
gcgctgaagc tgctgaaaga gtggggcagc ctggaaaaca tccagaaaaa cctggctcag     660
gtgaagccgg aacgtgttcg tgaggcgatt cgtaacaacc tggacaagct gcaaatgagc     720
ctggaactga ccgtctgcg taccgacctg ccgctggaag ttgatttccg tcgtcgtcgt     780
gaaccggatc gtgagggtct gggtgcgttc ctggaacgtc tggagtttgg tagcctgctg     840
cacgaatttg gcctcttaga atcacccaaa gccctggaag aagcactgtg gcctccacct     900
gaaggcgcct tgttggtttt gtttttgtct cgtaaagaac ctatgtgggc cgatttactg     960
gcctttagccg ctgcacgtgg tggtcgtgtc catcgcgcac cagaacctta taaagcactg    1020
cgtgatctta agaagctccg tggtctcctc gccaaagact tatccgtatt agcactccgc    1080
```

| gagggtttag | ggctgccacc | tggtgatgat | ccaatgttac | ttgcatatct | cctggatccc | 1140 |
| tctaatacaa | ccccggaagg | cgtggctcgt | cgttatggtg | atgaatggac | tgaagaagct | 1200 |
| ggtgaacgtg | cggctttgtc | tgaacgctta | ttcgctgacc | tgtggggccg | tctggaagga | 1260 |
| gaggaacgct | tactctggtt | atatcgtgaa | gttaacgcc | cactgtcagc | agtacttgcg | 1320 |
| cacatggaag | ctaccggggt | ccgcttagat | gttgcctatc | tccgtgctct | gagtcttgaa | 1380 |
| gtagccgaag | agattgcgcg | cctagaagcc | gaagtatttc | gtctggccgg | tcacccgttc | 1440 |
| aaccttaatt | cccgtgatca | actggaacgc | gttttgtttg | atgaacttgg | cctgcccgca | 1500 |
| attggtaaaa | ctgaaaaaac | tggtaaacgt | tcgacctccg | ccgcagtcct | tgaagccctg | 1560 |
| cgtgaagccc | acccaattgt | cgaaaaaatc | ctgcagtacc | gcgaactcac | taaacttaaa | 1620 |
| tctacctata | ttgacccgct | gccgcgtctg | gtgcacccga | aaaccggacg | tcttcacacc | 1680 |
| cgttttaatc | aaaactgctac | cgcgactgga | cgtttaagct | catccgatcc | caacttgcaa | 1740 |
| aatattcctg | tccgtacccc | actagggcaa | cgtattcgcc | gcgcatttat | cgcagaggaa | 1800 |
| ggttggttgc | tggtggcatt | agattatagc | caaattgaat | tacgtgttct | tgcgcattta | 1860 |
| tccggtgacg | aaaatctcat | tcgtgttttt | caggagggac | gtgatattca | cacagaaacc | 1920 |
| gcttcatgga | tgtttggtgt | tccgcgtgaa | gccgtcgacc | cgttaatgcg | tcgcgctgca | 1980 |
| aaaaccatta | atttcggtgt | tctgtatggt | atgagtgcac | atcggttatc | acaagaactc | 2040 |
| gctatcccgt | acgaagaagc | tcaagcattt | attgaacgtt | attttcagag | ttttcctaag | 2100 |
| gttcgtgcgt | ggatcgcgca | caccctggaa | gagggtcgta | agaaaggcta | cgtggagacc | 2160 |
| ctgttcggtc | gtcgtcgtta | cgttccggac | ctgaacgcgc | gtgtgaaaag | cgttcgtgaa | 2220 |
| gcggcggagc | gtatggcgtt | caacatggcg | gtgcaaggta | ccgcggcgga | cctgatgaag | 2280 |
| ctggcgatgg | tgaagctgtt | tccgcgtctg | ccggaagtgg | gtgcgcgtat | gctgctgcag | 2340 |
| gtgcacgatg | aactgctgct | ggaggcgccg | aaagagcgtg | cggaagaggc | ggcggcgctg | 2400 |
| gcgaaggaag | tgatggaggg | tgtttggccg | ctggcggtgc | cgctggaagt | ggaagttggt | 2460 |
| atcggtgaag | actggctgag | cgcgaagggc | taa | | | 2493 |

<210> SEQ ID NO 10
<211> LENGTH: 2545
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 10

| atgctgccgc | tgtttgagcc | gaaaggtcgt | gtgctgctgg | ttgacggtca | tcatctggcg | 60 |
| tatcgtaact | tctttacgct | gaaaggtctg | accaccagcc | gtggtgagcc | ggtgcaaggt | 120 |
| gtttacggct | tcgcgaaaag | cctggcgaag | gcgctgaaag | aagacggcga | tgtggttatc | 180 |
| gtggttttcg | acgcggaagc | gccgagcttt | cgtcacgagg | cgtacggtgc | gtataaagcg | 240 |
| ggtcgtgcgc | cgacccggga | ggacttcccg | cgtcagctgg | cgctgatgaa | ggaactggtg | 300 |
| gatctgctgg | gtctgaacg | tctggaagtt | ccgggctttg | aagcggatga | tgttctggcg | 360 |
| gcgctggcga | agatagcgga | acgtgagggt | tacgaagtgc | gtattctgac | cgcggaccgt | 420 |
| gacctgttcc | aactgctgag | cgaccgtatc | gcggttctgc | acccggaagg | tcacctgatt | 480 |
| accccgggct | ggctgtggga | gcgttatggt | ctcgtccgg | aacagtgggt | ggattttcgt | 540 |
| gcgctggcgg | gtgaccctag | cgataacatc | ccgggcgtta | aggtattagc | gagaagacc | 600 |

```
gcgctgaagc tgctgaaaga gtggggcagc ctggaaaaca tccagaaaaa cctggctcag    660
gtgaagccgg aacgtgttcg tgaggcgatt cgtaacaacc tggacaagct gcaaatgagc    720
ctggaactga gccgtctgcg taccgacctg ccgctggaag ttgatttccg tcgtcgtcgt    780
aaaccggatc gtgagggtct gcgtgcattc atggaacgtc tggagtttga tagcctgctg    840
cacgaatttg gcctcttaga atcacccaag gccctggaag aagcactgtg gcccccacct    900
gaaggcgcct tgttggtttt tgttttgtct cgtaaagaac ctatgtgggc cgatttactg    960
gccttagccg ctgcacgtgg tggtcgtgtc atcgcgcac cagaacctta taaagcactg   1020
cgtgatctta agaagctcg tggtctcctc gccaaagact tatccgtatt agcactccgc   1080
gagggtttag gctgccacc tggtgatgat ccaatgttac ttgcatatct cctggatccc   1140
tctaatacaa ccccggaagg cgtggctcgt cgttatggtg gtgaatggac tgaagaagct   1200
ggtgaacgtg cggctttgtc cgaacgctta ttcgctgacc tgtggggccg tctggaagaa   1260
gaggaacgct tactctggtt atatcatgaa gttgaacgcc cactgtcagc agtacttgcg   1320
cacatggaag ctaccggggt ccgcttagat gttgcctatc tccgtgctct gagtcttgaa   1380
gtagccgaag aaattgcgcg cctggaagcc gaagtatttc gtctggcggg ccacccgttt   1440
aacctgaaca gccgtgacca gctggaacgt gttctgtttg atgaactggg tctgccgccg   1500
atcggcaaga ccgagaaaac cggtaaacgt agcaccagcg cggcggtgct ggaagcgctg   1560
cgtgaggcgc acccgatcgt tgagaagatt ctgcaatacc gtgaactggc gaagctgaaa   1620
agcacctata ttgacccgct gccgcgtctg gtgcacccga aaaccggtcg tctgcacacc   1680
cgtttcaacc aaaccgcgac cgcgaccggc cgtctgagca gcagcgatcc gaacctgcag   1740
aacatcccgg ttcgtacccc gctgggtcaa cgtatccgta aggcgtttat cgcagaagaa   1800
ggttggctgc tggtggcatt agattatagc caaattgaac tgcgtgttct ggcgcacctg   1860
agcggtgacg agaacctgat ccgtgtgttc cgtgaaggca agatattca ccgagacc   1920 gcttcatgga tgtttggtgt tccgcgtgaa gccgtcgacc gttaatgcg tcgcgctgca   1980 aaaaccatta ttttggtgt tctgtatggt atgagcgcgc accgtctgag ccaggaactg   2040
agcatcccgt atgaagaggc ggcggcgttt attgagcgtt atttccagcg ctttccgcaa   2100
gtgcgtgcgt ggatcgcgca caccctggaa gagggtcgta agaaaggcta cgtggagacc   2160
ctgttcggtc gtcgtcgtta cgttccggac ctgaacgcgc gtgtgaaaag cgttcgtgaa   2220
gcagcggagc gtatggcgtt caacatggcg gtgcaaggta ccgcggcgga cctgatgaag   2280
ctggcgatgg tgaagctgtt tccgcgtctg cgtccgctgg cgttcgtat gctgctgcag   2340 gttcacgatg aactgctgct ggaggcgccg aaagagcgtg cggaagaggc ggcggcgctg   2400
gcgaaggaag tgatggaggg tgtttggccg ctggcggtgc cgctggaagt ggaagttggt   2460
atcggtgaag actggctgag cgcgaagggc taatatctaa ctaagcttga cctgtgaagt   2520
gaaaaatggc gcacatggcg acatt                                         2545
```

<210> SEQ ID NO 11
<211> LENGTH: 2493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgctgccgc tgtttgagcc gaaaggtcgt gtgctgctgg ttgacggtca tcatctggcg     60
```

| | |
|---|---|
| tatcgtaact tctttacgct gagaggtctg accaccagcc gtggtgagcc tgtgcaaggt | 120 |
| gtttacggct tcgcgaaaag cctggcgaag gcgctgaaag aagacggcga tgtggttatc | 180 |
| gtggttttcg acgcgaaagc gccgagcttt cgtcacgagg cgtacggtgc gtataaagcg | 240 |
| ggtcgtgcgc cgaccccgga ggacttcccg cgtcagctgg cgctgatgaa ggaactggtg | 300 |
| gatctgctgg gtctggagcg tctggaagtt ccgggccttg aagcggatga tgttttggcg | 360 |
| gcgctggcga agatagcgga acgtgagggt tacgaagtgc gtattctgac cgcggaccgt | 420 |
| gacctgttcc aactgctgag cgaccgtatc gcggttctgc acccggaagg tcacctgatt | 480 |
| accccgggct ggctgtggga cgttatggt ctgcgtccgg aacagtgggt ggattttcgt | 540 |
| gcgctgacgg gtgacccgag cgataacatc ccgggcgtta aggtattggc gagaagacc | 600 |
| gcgctgaagc tgctgaaaga gtggggcagc ctggaaaaca tccagaaaaa cctggatcag | 660 |
| gtgaagccgg aacgtgttcg tgaggcgatt cgtaacaacc tggacaagct gcaaatgagc | 720 |
| ctggaactga ccgtctgcg taccgacctg ccgctggaag ttgatttccg tcgtcgtcgt | 780 |
| gaaccggatc gtgagggtct gcgtgcgttc ctgaacgtc tggagtttgg tagcctgctg | 840 |
| cacgaatttg gcctcttaga atcacccaag gccctggaag aagcactgtg gcctccacct | 900 |
| gaaggcgcct ttgttggttt tgttttgtct cgtaaagaac ctatgtgggc cgatttactg | 960 |
| gccttagccg ctgcacgtgg tggtcgtgtc catcgcgcac cagaaccta taaagcactg | 1020 |
| cgtgaccta aagaagctcg tggtctcctc gccaaagact tatccgtatt agcactccgc | 1080 |
| gagggtttag gctgccacc tggtgatgat ccaatgttac ttgcatatct cctggatccc | 1140 |
| tctaatacaa ccccggaagg cgtggctcgt cgttatggtg gtgaatggac tgaagaagct | 1200 |
| ggtgaacgtg cggctttgtc tgaacgctta ttcgctaacc tgtggagccg tctggaagga | 1260 |
| gaggaacgct tactctggtt atatcgtgaa gttaacgcc cactgtcagt agtactagcg | 1320 |
| cacatggaag ctaccggggt ccgcttagat gttgcctatc tccgtgctct gagtcttgaa | 1380 |
| gtagccgaag aaattgcgcg cctggaagcc gaagtatttc gtctggcggg ccacccgttt | 1440 |
| aacctgaaca gccgtgacca gctggaacgt gttctgtttg atgaactggg tctgccgccg | 1500 |
| atcggcaaga ccgagaaaac cggtaaacgt agcaccagcg cggcggtgct ggaagcgctg | 1560 |
| cgtgaggcgc acccgatcgt tgagaagatt ctgcaatacc gtgaactggc gaagctgaaa | 1620 |
| agcacctata ttgaccccgct gccgcgtctg gtgcacccga aaaccggtcg tctgcacacc | 1680 |
| cgtttcaacc aaaccgcgac cgcgaccggc cgtctgagca gcagcgatcc gaacctgcag | 1740 |
| aacatcccgg ttcgtacccc gctgggtcaa cgtatccgta aggcgtttat cgcagaagaa | 1800 |
| ggttggctgc tggtggcatt agattatagc caaattgaac tgcgtgttct ggcgcacctg | 1860 |
| agcggtgacg agaacctgat ccgtgtgttc cgtgaaggca agatattca caccgagacc | 1920 |
| gcttcatgga tgtttggtgt tccgcgtgaa gccgtcgacc cgttaatgcg tcgcgctgca | 1980 |
| aaaaccatta tttttggtgt tctgtatggt atgagtgcac atcggttatc acaagaactc | 2040 |
| gctatcccgt atgaagaagc tcaagcattt attgaacgtt attttcagag ttttcctaag | 2100 |
| gttcgtgctt ggattgaaaa acattggaa gagggtcgtc agcgtggcta cgtggaaacc | 2160 |
| ctgtttggtc gtcgtcgtta cgttccggat ctgaacgcgc gtgtgaaaag ggttcgtgaa | 2220 |
| gcggcggagc gtatggcgtt caacatgccg gttcaaggta ccgcggcgga cctgatgaag | 2280 |
| ctggcgatgg ttcgtctgtt cccgcgtctg ccggaagtgg gtgcgcgtat gctgctgcag | 2340 |
| gttcacgatg aactgctgct ggaggcgccg aaagagcgtg cggaagaggc ggcggcgctg | 2400 |
| gcgagggaag tgatggaggg tgtttggccg ctggcggtgc cgctggaagt ggaagttggt | 2460 |

```
attggtgaag actggctgag cgcgaagggc taa                           2493
```

<210> SEQ ID NO 12
<211> LENGTH: 2493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgctgccgc tgtttgagcc gaaaggtcgt gtgctgctgg ttgacggtca tcatctggcg     60
tatcgtaact tctttacgct gaaaggtccg accaccagcc gtggtgagcc ggtgcaaggt    120
gtttacggct cgcgaaaaag cctggcgaag gcgctgaaag aagacggcga tgtggttatc    180
gtggttttcg acgcgaaagc gccgagcttt cgtcacgaga cgtacggtgc gtataaagcg    240
ggtcgtgcgc cgaccccgga ggacttcccg cgtcagctgg cgctgatgaa ggaactggtg    300
gatctgctgg gtctggagcg tctggaagtt ccgggctttg aagcggatga tgttctggcg    360
gcgctggcga agatagcgga gcgtgagggt tacgaagtgc gtattctgac cgcggaccgt    420
gacctgttcc aactgctgag cgaccgtatc gcggttctgc acccggaagg tcacctgatt    480
accccgggct ggctgtggga gcgttatggt ctgcgtccgg aacagtgggt ggattttcgt    540
gcgctggcgg gtgacccgag cgataacatc ccgggcgtta aggtattggc gagaagacc    600
gcgctgaagc tgctgaaaga gtggggcagc ctggaaaaca tccagaaaaa cctggatcag    660
gtgaagccgg aacgtgttcg tgaggcgatt cgtaacaacc tggacaagct gcaaatgagt    720
ctggaactga ccgtctgcg taccgacctg ccgctggaag ttgatttccg tcgtcgtcgt    780
gaaccggatc gtgagggtct gcgtgcgttc ctggaacgtc tggagtttgg tagcctgctg    840
cacgaatttg gcctcttaga atcacccaag gccctggaag aagcactgtg gcctccacct    900
gaaggcgcct ttgttggttt tgttttgtct cgtaaagaac ctatgtgggc cgatttactg    960
gccttagccg ctgcacgtgg tggtcgtgtc catcgcgcac cagaaccttac taaagcactg   1020
cgtgaccttaa agaagctcg tggtctcctc gccaaagact tatccgtatt agcactccgc   1080
gagggtttag gctgccacc tggtgatgat ccaatgttac ttgcatatct cctggatccc   1140
tctaatacaa ccccggaagg cgtggctcgt cgttatggtg gtgaatggac tgaagaagct   1200
ggtgaacgtg cggctttgtc tgaacgctta ttcgctaacc tgtggggccg tctggaagga   1260
gaggaacgct tactctggtt atatcgtgaa gttgaacgcc cactgtcagc agtacttgcg   1320
cacatggaag ctaccggggt ccgcttagat gttgcctatc tccgtgctct gagtcttgaa   1380
gtagccgaaa aaattgcgcg cctggaagcc gaagtatttc gtctggcggg ccacccgttt   1440
aacctgaaca gccgtgacca gctggaacgt gttctgtttg atgaactggg tctgccgccg   1500
atcggcaaga ccgagaaaac cggtaaacgt agcaccagcg cggcggtgct ggaagcgctg   1560
cgtgaggcgc acccgatcgt tgagaagatt ctgcaatacc gtgaactggc gaagctgaaa   1620
agcacctata ttgacccgct gccgcgtctg gtgcacccga aaccggtcg tctgcacacc   1680
cgtttcaacc aaaccgcgac cgcgaccggc cgtctgagca gcagcgatcc gaacctgcag   1740
aacatcccgg ttcgtacccc gctgggtcaa cgtatccgta aggcgtttat cgcagaagaa   1800
ggttggctgc tggtggcatt agattatagc caaattgaac tgcgtgttct ggcgcacctg   1860
agcggtgacg agaacctgat ccgtgtgttc cgtgaaggca agatattca caccgagacc   1920
gcggcgtgga tgtttggtgt gccgccggaa ggtgttgatg gtgcgatgcg tcgtgcggcg   1980
```

```
aagaccgtga acttcggtgt tctgtatggc atgagcgcgc accgtctgag ccaggaactg    2040
agcatcccgt acgaagaggc ggcggcgttt attgagcgtt atttccagcg ctttccgcaa    2100
gtgcgtgcgt ggatcgcgca caccctggaa gagggtcgta agaaaggcta cgtggagacc    2160
ctgttcggtc gtcgtcgtta cgttccggac ctgaacgcgc gtgtgaaaag cgttcgtgaa    2220
gcagcggagc gtatggcgtt caacatggcg gtgcaaggta ccgcggcgga cctgatgaag    2280
ctggcgatgt gaagctgtt tccgcgtctg ccggaagtgg gtgcgcgtat gctgctgcag    2340
gtgcacgatg aactgctgct ggaggcgccg aaagagcgtg cggaagaggc ggcggcgctg    2400
gcgaaggaag tgatggaggg tgtttggccg ctggcggtgc cgctggaagt ggaagttggt    2460
atcggtgaag actggctgag cgcgaagggc taa                                 2493
```

<210> SEQ ID NO 13
<211> LENGTH: 2493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atgctgccgc tgtttgagcc gaaaggtcgt gtgctgctgg ttgacggtca tcatctggcg      60
tatcgtaact tctttacgct gaaaggtctg accaccagcc gtggtgagcc tgtgcaaggt     120
gtttacggct cgcgaaaaag cctggcgaag gcgctgaaag aagacggcga tgtggttatc     180
gtggttttcg acgcgaaagc gccgagcttt cgtcacgagg cgtacggtgc gtataaagcg     240
ggtcgtgcgc cgaccccgga ggacttcccg cgtcagctgg cgctgatgaa ggaactggtg     300
gatctcctgg gtctggagcg tctggaagtt ccgggctttg aagcggatga tgttctggcg     360
gcgctggcga agatagcgga acgtgagggt tacgaagtgc gtattctgac cgcggaccgt     420
gacctgttcc aactgctgag cgaccgtatc gcggttctgc acccggaagg tcacctaatt     480
accccgggct ggctgtggga cgttatggt ctgcgtccgg aacagtgggt gaattttcgt     540
gcgctggcgt gtgaccccgag cgataacatc ccgggcgtta aggtattggc gagaagacc     600 acgctgaagc tgctgaaaga gtggggcagc ctggaaaaca tccagaaaaa cctggatcag     660
gtgaagccgg aacgtgttcg tgaggcgatt cgtaacaacc tggacaagct gcaaatgagc     720
ctggaactga gctgtctgcg taccgacctg ccgctggaag ttgatttccg tcgtcgtcgt     780
gaaccggatc gtgagggtct gcgtgcgttc ctggaacgtc tggagtttgg tagcctgctg     840
cacgaatttg gcctcttaga gtcacccaag gccctggaag aagcactgtg gcctccacct     900
gaaggcgcct tgttggtttt gttttgtct cgtaaagaac ctatgtgggc cgatttactg     960
gccttagccg ctgcacgtgg tggtcgtgtc catcgcgcac cagaaccta taaagcactg    1020 cgtgatctta agaagctcg tggtctcctc gccaaagact tatccgtatt agcactccgc    1080
gagggtttag gctgccacc tggtgatgat ccaatgttac ttgcatatct cctggatccc    1140
tctaatacaa ccccggaagg cgtggctcgt cgttatggtg gtgaatggac tgaagaagct    1200
ggtgaacgtg cggctttgtc tgaacgctta ttcgctaacc tgtggggccg tctgaaggga    1260
gaggaacgct tactctggtt atatcgtgaa gttgaacgcc cactgtcagc agtacttgcg    1320
cacatggaag ctaccggggt ccgcttagat gttgcctatc tccgtgctct gagtcttgaa    1380
gtagccgaag aaattgcgcg cctggaagcc gaagtatttc gtctggcggg ccacccgttt    1440
aacctgaaca gccgtgacca gctggaacgt gttctgtttg atgaactggg tctgccgccg    1500
```

```
atcggcagga ccgagaaaac cggtaaacgt agcaccagcg cggcggtgct ggaagcgctg    1560
cgtgaggcgc acccgatcgt tgagaagatt ctgcaatacc gtgaactggc gaagctgaaa    1620
agcacctata ttgacccgct gccgcgtctg gtgcacccga aaaccggtcg tctgcacacc    1680
cgtttcaacc aaaccgcgac cgcgaccggc cgtctgagca gcagcgatcc gaacctgcag    1740
aacatcccgg ttcgtacccc gctgggtcaa cgtatccgta aggcgtttat cgcagaagaa    1800
ggttggctgc tggtggcatt agattatagc caaattgaac tgcgtgttct ggcgcacctg    1860
agcggtgacg agaacctgat ccgtgtgttc cgtgaaggca agatattca caccgagacc    1920 gcttcatgga tgtttggtgt tccgcgtgaa gccgtcgacc cgttaatgcg tcgcgctgca    1980
aaaaccatta attttggtgt tctgtatggt atgagcgcgc accgtctgag ccaggaactg    2040
agcatcccgt atgaagaggc ggtggcgttt attgagcgtt atttccagag ctttccgcaa    2100
gtgcgtgcgt ggatcgcgca cccctggaa gagggtcgta agaaaggcta cgtggagacc    2160
ctgttcggtc gtcgtcgtta cgttccggac ctgaacgcgc gtgtgaaaag cgttcgtgaa    2220
gcggcggagc gtatggcgtt caacatggcg gtgcaaggta ccgcggcgga cctgatgaag    2280
ctggcgatgg tgaagctgtt tccgcgtctg ccggaagtgg gtgcgcgtat gctgctgcag    2340
gtgcacgatg aactgctgct ggaggcgccg aaagagcgtg cggaagaggc ggcggcgctg    2400
gcgaaggaag tgatggaggg tgtttggccg ctggcggtgc cgctggaagt cgaagtgggc    2460
atcggtgaag actggctgtc ggcaaaagaa taa                                2493

<210> SEQ ID NO 14
<211> LENGTH: 2502
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
tatgctgccg ctgtttgagc cgaaaggtcg tgtgctgctg gttgacggtc atcatctggc     60
gcatcgtaac ttcttcgcgc tgaaaggtct gaccaccagc cgtggtgagc cggtgcaagg    120
tgtttacggc ttcgcgaaaa gcctgctgaa ggcgctgaaa aagacggcg atgtggttat    180 cgtggttttc gacgcgaaag cgccgagctt cgtcacgag gcgtacggtg cgtataaagc    240
aggtcgtgcg ccgaccccgg aagacttccc gcgtcaactg gcgctgatta aggagctggt    300
tgatctgctg ggtctggtgc gtctggaagt gccgggcttt gaagcggatg atgtgctggc    360
gaccctggcg aagaaagcag aaaagaagg atatgaagta cgcatcctga cagccgacaa    420
agacttatac caaatccttt cagatcgcgt ccacgtttta catcccgaag gtacttaat    480 taccctgca tggctgtggg aaaatatgg attacgtccg gatcaatggg ccgattaccg    540
tgctttaacc ggtgatgaat cagataacct gccagatgtt aaaggattg gagaaaaaac    600 tgcctgtaaa ttgttagatg aatggggctc tttggaagca ctgttaaaaa accttgatcg    660
tctcaaacct gccatccgcg aaaaaatcct ggcccacatg gatgacttaa aactgagctg    720
ggatcccgct aaagttcgta ccgacttacc tcttgaagtt gattttgcaa acgccgtga    780 acctgatcgt gaacgccttc gtgcatttct tgaacgtctg gaatttggct ccttgttaca    840
tgaatttggc ctcttagaat cacccaaggc cctggaagaa gcactgtggc ctccacctga    900
aggcgccttt gttggttttg ttttgtctcg taaagaacct atgtgggccg atttactggc    960
attagccgct gcacgtggtg gtcgtgtcca tcgcgcacca gaaccttata agcactgcg    1020
```

```
tgatcttaaa gaagctcgtg gtctcctcgc caaagactta tccgtattag cactccgcga    1080
gggtttaggg ctgccacctg gtgatgatcc aatgttactt gcatatctcc tggatccctc    1140
taatacaacc ccggaaggcg tggctcgtcg ttatggtggt gaatggactg aagaagctgg    1200
tgaacgtgcg gctttgtctg aacgcttatt cgctgacctg tggggccgtc tggaaggaga    1260
ggaacgctta ctctggttat atcgtgaagt tgaacgccca ctgtcagcag tacttgcgcg    1320
catggaagct accggggtcc gcttagatgt tgcctatctc cgtgctctga gtcttgaagt    1380
agccgaagaa attgcgcgcc tggaagccga agtatttcgt ctggccggtc acccgtttaa    1440
ccttaattcc cgtgatcaac tggaacgcgt tttgtttgat gaacttggcc tgcccgcaat    1500
tggtaaaact gaaaaaactg gtaaacgttc gacctccgcc gcagtccttg aagccctgcg    1560
tgaagcccac ccaattgtcg aaaaaatcct gcagtaccgg gaactcacga aacttaaatc    1620
tacctatatt gacccgctgc cgcgtctggt gcacccgaaa accggacgtc ttcacacccg    1680
ttttaatcaa actgctaccg cgactggacg tttaagctca tccgatccca acttgcaaaa    1740
tattcctgtc cgtaccccac tagggcaacg tattcgtaag gcgtttattg cggaagaggg    1800
ccacctgctg gttgcgctgg actacagcca gatcgaactg cgtgttctgg cgcacctgag    1860
cggtgacgag aacctgatcc gtgttttcca ggaaggcaaa gatattcaca ccgagaccgc    1920
ggcgtggatg tttggtgtgc cgccggaagg tgttgatggt gcgatgcgtc gtgcggcgaa    1980
gaccgtgaac ttcggtgttc tgtatggcat gagcgcgcac cgtctgagcc aggaactgag    2040
catcccgtac gaagaggcgg cggcgtttat tgagcgttat ttccagagct ttccgcaagt    2100
gcgtgcgtgg atcgcgcaca ccctggaaga gggtcgtaag aaaggctacg tggagaccct    2160
gttcggtcgt cgtcgttacg ttccggacct gaacgcgcgt gtgaaaagcg ttcgtaaagc    2220
ggcggagcgt atggcgttca acatggcggt gcaaggtacc gcggcggacc tgatgaagct    2280
ggcgatggtg aagctgtttc gcgtctgcc ggaagtgggt gcgcgtatgc tgttgcaggt    2340
gcacgatgaa ctgctgctgg aggcgccgaa agagcgtgcg gaagaggcgg cggcgctggc    2400
gaaggaagtg atggagggtg tttggccgct tgcggtgccg ctggaagtgg aagttggtat    2460
cggtgaagac tggctgagcg cgaagggcta atatctaact aa                      2502
```

<210> SEQ ID NO 15
<211> LENGTH: 2490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgctgccgc tgtttgagcc gaaaggtcgt gtgctgctgg ttgacggcca ccacctggcg      60
taccgtacct tctttgcgct gaaaggtctg accaccagcc gtggtgagcc ggtgcaaggt     120
gtttacggct tcgcgaaaag cctgctgaag gcgctgaaaa agacggcga ggtggcgatc      180 gtggttttcg atgcgaaagc gccgagcttt cgtcacgaag cgtacgaggc gtataaagcg     240
ggtcgtgcgc cgacccccgga agacttcccg cgtcaactgg cgctgattaa ggagctggtt    300
gatctgctgg gtctggtgcg tctggaagtg ccgggctttg aagcggatga tgttctggcg    360
gcgctggcga gaaagcgga acgtgagggt tacgaggttc gtatcctgag cgcggaccgt    420
gatctgtatc agctgctgag cgaccgtatt cacctactgc atcccgaagg ctacttaatt    480
acccctgcat ggctgtggga aaaatatgga ttacgtccgg atcaatgggc cgattaccgt    540
```

```
gctttaaccg gtgatgaatc agataacctg ccaggtgtta aagggattgg agaaaaaact    600
gcccgtaaat tgttagaaga atggggctct ttggaagcac tgttaaaaaa ccttgatcgt    660
ctcaaacctg ccatccgcga aaaaattctg gcccacatgg atgacttaaa actgagctgg    720
gatcccgcta aagttcgtac cgacttacct ctcgaagttg attttgcaaa acgccgtgaa    780
cctgatcgtg aacgccttcg tgcatttctt gaacgtctgg aatttggctc cttgttacac    840
gaatttggcc tcttagaatc acccaaggcc ctggaagaag caccgtggcc tccacctgaa    900
ggcgcctttg ttggttttgt tttgtctcgt aaagaaccta tgtgggccga tttactggcc    960
ttagccgctg cacgtggtgg tcgtgtccat cgcgcaccag aaccttataa agcactgcgt   1020
gatcttaaag aagctcgtgg tctcctcgcc aaagacttat ccgtattagc actccgcgag   1080
ggtttagggc tgccacctgg tgatgatcca atgttacttg catatctcct ggatccctct   1140
aatacaaccc cggaaggcgt ggctcgtcgt tatggtggtg aatggactga agaagctggt   1200
gaacgtgcgg ctttgtctga acgcttattc gctaacctgt ggggccgtct ggaaggagag   1260
gaacgcttac tctggttata tcgtgaagtt gaacgcccac tgtcagcagt acttgcgcac   1320
atggaagcta ccggggtccg cttagatgtt gcctatctcc gtgctctgag tcttgaagta   1380
gccgaagaaa ttgcgcgcct ggaagccgaa gtatttcgtc tggccggtca cccgttcaac   1440
cttaattccc gtgatcaact ggaacgcgtt ttgtttgatg aacttggcct gcccgcaatt   1500
ggtaaaactg aaaaaactgg taaacgttcg acctccgccg cagtccttga gccctgcgt   1560
gaagcccacc caattgtcga aaaaatcctg cagtaccgcg aactcactaa acttaaatct   1620
acctatattg acccgctgcc gcgtctggtg cacccgaaaa ccggacgtct tcacacccgt   1680
tttaatcaaa ctgctaccgc gactggacgt ttaagctcat ccgatcccaa cttgcaaaat   1740
attcctgtcc gtaccccact agggcaacgt attcgccgcg catttatcgc agaggaaggt   1800
tggttgctgg tggcattaga ttatagccaa attgaattac gtgttcttgc gcatttatcc   1860
ggtgacgaaa atctcattcg tgtttttcag gagggacgtg atattcacac agaaaccgct   1920
tcatggatgt ttggtgttcc gcgtgaagcc gtcgacccgt taatgcgtcg cgctgcaaaa   1980
accattaatt tcggtgttct gtatggtatg agtgcacatc ggttatcaca agaactcgct   2040
atcccgtacg aagaagctca agcatttatt gaacgttatt ttcagagttt tcctaaggtt   2100
cgtgcttgga ttgagcgtac cctggaagag ggtcgtcagc gtggctacgt ggaaaccctg   2160
tttggtcgtc gtcgttacgt tccggatctg aacgcgcgtg tgaaagggt tcgtaaagcg   2220
gcggagcgta tggcgttcaa catgcaggtg caaggtaccg cggcggacct gatgaagctg   2280
gcgatggttc gtctgttccc gcgtctgccg gaagtgggtg cgcgtatgct gctgcaggtt   2340
cacgatgaac tgctgctgga ggcgccgaaa gagcgtgcgg aagaggcggc gcaactggcg   2400
aaggaaacca tggagggtgt ttggccgctg gcggtgccgc tggaagtcga agtgggcatc   2460
ggtgaagact ggctgtcggc aaaagaataa                                    2490
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 16

His His His His His His

```
<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaaggtgaag gtcggagtc                                                    19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaagatggtg atgggatttc                                                   20
```